United States Patent
Magistrelli et al.

(10) Patent No.: US 10,113,193 B2
(45) Date of Patent: Oct. 30, 2018

(54) METHOD FOR OPTIMIZING THE ASSEMBLY AND PRODUCTION OF HETERO-MULTIMERIC PROTEIN COMPLEXES

(71) Applicant: NovImmune SA, Geneva (CH)

(72) Inventors: Giovanni Magistrelli, Cessy (FR); Pauline Malinge, Cernex (FR); Yves Poitevin, Ambilly (FR); Nicolas Fischer, Geneva (CH)

(73) Assignee: NovImmune SA, Geneva (CH)

( * ) Notice: Subject to any disclaimer, the term of this patent is extended or adjusted under 35 U.S.C. 154(b) by 397 days.

(21) Appl. No.: 15/086,736

(22) Filed: Mar. 31, 2016

(65) Prior Publication Data

US 2016/0289727 A1 Oct. 6, 2016

Related U.S. Application Data

(60) Provisional application No. 62/141,009, filed on Mar. 31, 2015.

(51) Int. Cl.

| | |
|---|---|
| *C12P 21/00* | (2006.01) |
| *C07K 16/18* | (2006.01) |
| *C07K 16/46* | (2006.01) |
| *C12P 21/02* | (2006.01) |
| *C12N 15/85* | (2006.01) |
| *C12N 15/67* | (2006.01) |

(52) U.S. Cl.
CPC ............ *C12P 21/005* (2013.01); *C07K 16/18* (2013.01); *C07K 16/468* (2013.01); *C12N 15/67* (2013.01); *C12N 15/85* (2013.01); *C12P 21/02* (2013.01); *C07K 2317/31* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel |
| 4,551,433 A | 11/1985 | De Boer |
| 4,560,655 A | 12/1985 | Baker |
| 4,657,866 A | 4/1987 | Kumar |
| 4,767,704 A | 8/1988 | Cleveland |
| 4,927,762 A | 5/1990 | Darfler |
| 5,654,173 A | 8/1997 | Jacobs |

FOREIGN PATENT DOCUMENTS

| | | |
|---|---|---|
| EP | 0036776 | 9/1981 |
| WO | WO 8700195 | 6/1986 |
| WO | WO 2012023053 | 2/2012 |

OTHER PUBLICATIONS

Barnes et al., "Methods for Growth of Cultured Cells in Serum-Free Medium" Anal. Biochem. vol. 102, p. 255-270 (1980).
Benoist et al., "In vivo sequence requirements of the SVB40 early promoter region" Nature vol. 290, p. 304-310 (1981).
Boshart et al., "A Very Strong Enhancer is Located Upstream of an Immediate Early Gene of Human Cytomegalovirus", Cell, vol. 41, p. 521-530 (1985).
Bowie et al. "A Method to Identify Protein Sequences that Fold into a Known Three-Dimensional Structure" Science, vol. 253, p. 164-170 (1991).
Carton et al. "Codon engineering for improved antibody expression in mammalian cells", Protein Expression and Purification, vol. 55, No. 2, p. 279-286, (2007).
Chadwick, et al, "Safety of a single aerosol administration of escalating doses of the cationic lipid GL-67/DOPE/DMPE-PEG5000 formulation to the lungs of normal volunteers" Gene Therapy, vol. 4, p. 937-942 (1997).
Chang et al., "Phenotypic expression in *E.coli* of a DNA Sequence coding for mouse dihydrofolate reductase" Nature, vol. 275, p. 617-624 (1978).
Deboer et al., "The tac promoter: A functional hybrid derived from the trp and lac promoters" Proc. Natl. Acad. Sci. (USA) vol. 80, p. 21-25 (1983).
Dijemka et al., "Cloning and expression of the chromosomal immune interferon gene of the rat" EMBO J., vol. 4, p. 761-767 (1985).
Fischer et al., "Exploiting light chains for the scalable generation and platform purification of native human bispecific IgG" Nature Communications, vol. 6, p. 6113 (2015).
Gao et al. "Cationic Liposome-mediated gene transfer", Gene Therapy. vol. 2, p. 710-722, (1995).
Goddard, et al, "A second dose of a CFTR cDNA—liposome complex is as effective as the first dose in restoring cAMPdependent chloride secretion to null CF mice trachea" Gene Therapy, vol. 4, p. 1231-1236 (1997).
Goeddel et al., "Direct Expression in *Escherichia coli* of a DNA sequence coding for human growing hormone" Nature, vol. 281, p. 544-548 (1979).
Goeddel et al. "Synthesis of human fibroblast interferon by *E. coli*", Nucleic Acids Res. vol. 8, p. 4057-4074 (1980).
Gokhale et al, "Antisense raf oligodeoxyribonucleotide is protected by liposomal encapsulation and inhibits Raf-1 protein expression in vitro and in vivo: implication for gene therapy of radioresistant cancer" Gene Therapy, vol. 4, p. 1289-1299 (1997).

(Continued)

*Primary Examiner* — Suzanne M Noakes
*Assistant Examiner* — Jae W Lee
(74) *Attorney, Agent, or Firm* — Cooley LLP; Ivor R. Elrifi; Cynthia Kozakiewicz

(57) ABSTRACT

Methods are provided to improve the expression of protein complexes by tuning the expression levels of each component required for the assembly of the complex. These methods are effective in limiting the expression of the dominant chain and, thus, equilibrating their relative abundance. The methods provided herein lead to a significant increase in productivity and final bispecific yields both in transient expression systems as well as in stably transfected mammalian cells.

11 Claims, 8 Drawing Sheets

Specification includes a Sequence Listing.

(56) References Cited

OTHER PUBLICATIONS

Gorman et al., "The Rous sarcoma virus long terminal repeat is a strong promoter when introduced into a variety of eukaryotic cells by DNA-mediated transfection" Proc. Natl. Acad. Sci. (USA) vol. 79, p. 6777 (1982).

Gorman et al, "Efficient in vivo delivery of DNA to pulmonary cells using the novel lipid EDMPC" Gene Therapy, vol. 4, p. 983-992 (1997).

Ham et al., "Media and Growth Requirements" Meth. Enz., vol. 58, p. 44 (1979).

Hamer et al., "Regulation In Vivo of a Cloned Mammalian Gene: Cadmium Induces the Transcription of a Mouse Metallothionein Gene in SV40 Vectors" J. Mol. Appl. Gen., vol. 1, p. 273-288 (1982).

Johnston et al., "Isolation of the yeast regulatory gene GAL4 and analysis of its dosage effects on the galactose/melibiose regulon" Proc. Natl. Acad. Sci. (USA), vol. 79, p. 6971-6975 (1982).

Kontermann R. et al. "Bispecific antibodies", Drug Discover Today, (2015), available at dx.doi.org/10.1016/j.drudis.2015.02.2008.

McKnight, "Functional Relationships between Transciptional Control Signals of the Thymidine Kinase Gene of Herpes Simplex Virus" Cell, vol. 31, p. 355-365 (1982).

Meng J. et al. "Refining the balance of attenuation and immunogenicity of respiratory syncytial virus by targeted codon deoptimization of virulence genes", MBIO, vol. 5, No. 5, p. 1-10 (2014).

Monahan, "Direct intramuscular injection with recombinant AAV vectors results in sustained expression in a dog model of hemophilia" et al, Gene Therapy, vol. 4, p. 40-49, (1997).

Onodera, et al, "Successful Peripheral T-Lymphocyte—Directed Gene Transfer for a Patient With Severe Combined Immune Deficiency Caused by Adenosine Deaminase Deficiency" Blood, vol. 91, p. 30-36 (1998).

Siebenlist et al., "*E. Coli* RNA Polymerase Interacts Homologously with Two Different Promoters" Cell, vol. 20, p. 269-281 (1980).

Silver et al., "Amino terminus of the yeast GAL4 gene product is sufficient for nuclear localization" Proc. Natl. Acad. Sci. (USA), vol. 81, p. 5951-5955 (1984).

Spiess C. et al. "Alternative molecular formats and therapeutic applications for bispecific antibodies" Molecular Immunology, vol. 67, No. 2, p. 95-106 (2015).

Strutzenberger et al., "Changes during subclone development and ageing of human antibody-producing recombinant CHO cells", J. Biotechnol., vol. 69(2-3), p. 215-226 (1999).

Thornton et al. "Prediction of progress at last" Nature, vol. 354, p. 105 (1991).

Westwood A. et al. "Improved recombinant protein yield using a codon deoptimized DHFR selectable marker in a CHEF1 expression plasmid", Biotechnology Progress, vol. 26, No. 6, p. 1558-1566 (2010).

METHOD FOR OPTIMIZING THE ASSEMBLY AND PRODUCTION OF HETERO-MULTIMERIC PROTEIN COMPLEXES

RELATED APPLICATION

This application claims the benefit of U.S. Provisional Application No. 62/141,009, filed Mar. 31, 2015, the contents of each of which are incorporated herein by reference in their entireties.

The contents of the text file named "NOVI039001US_ST25.txt", which was created on Jun. 7, 2016 and is 17.3 KB in size, are hereby incorporated by reference in their entirety.

FIELD OF THE INVENTION

Methods are provided to improve the expression of protein complexes by tuning the expression levels of each component required for the assembly of the complex. These methods are effective in limiting the expression of the dominant chain and, thus, equilibrating their relative abundance. The methods provided herein lead to a significant increase in productivity and final bispecific yields both in transient expression systems as well as in stably transfected mammalian cells.

BACKGROUND OF THE INVENTION

Recombinant expression in bacterial, yeast, insect, plant or mammalian cells is fundamental for the production of proteins that are used for research as well as therapeutic applications. Recently, the yield of recombinant protein expression in Chinese Hamster Ovary (CHO) cells has been significantly enhanced by optimizing multiple parameters such as culture medium composition, fermentation parameters, as well as optimization of the constructs that are used to drive the expression of the gene encoding the recombinant protein of interest.

Some proteins are composed of several polypeptides that can associate in complexes that can be covalently or non-covalently linked. Antibodies are an example of such a class of proteins as they are composed of four polypeptides (i.e. two heavy chains and two light chains) that are linked by disulfide bonds. Due to their commercial and therapeutic importance, the expression of antibodies in CHO cells has been the subject of intense efforts of optimization, aiming at maximizing the expression of the two chains that compose the antibody. However, major differences can be observed as the levels of expression can vary up to 200-fold between antibodies.

Previous optimization approaches aimed at increasing the expression levels of polypeptides in order to achieve higher production yields. In the case of protein complexes composed of multiple polypeptides, unbalanced expression can limit assembly of the desired molecule, promote production of unwanted products and limit the overall production yield. Accordingly, there exists a need for methods for improving expression of protein complexes.

SUMMARY OF THE INVENTION

The methods of the disclosure improve the expression of protein complexes by tuning the expression levels of each component required for the assembly of the complex. In contrast to previously described approaches, reducing the expression of one or several polypeptides in the protein complex enhances the assembly and yield of the protein complex. The method is particularly suited to optimize the expression and yield of bispecific antibodies that often rely on the co-expression of multiple polypeptides. The unbalanced expression (too high or too low) of one of the components can lead to a significant decrease of the desired final product and an increase in the production of unwanted side-products. This limitation can impact both IgG-like bispecific formats as well as formats based on antibody fragments.

The method is in particular applicable for the optimization of the expression of bispecific antibodies named KA-bodies (Fischer et al., Exploiting light chains for the scalable generation and platform purification of native human bispecific IgG. Nat. Comms, 6: 6113 (2015)). This technology produces a fully-human bispecific antibody (BsAb), composed of a common heavy chain and two different light chains (one kappa and one lambda) (see e.g., WO 2012/023053). A proprietary tricistronic vector including these three chains is introduced in mammalian cells to produce the bispecific antibodies (κλ-bodies) that contain one κ and one λ chains in addition to the two monospecific antibodies IgGκ and IgGλ.

In principle, if the two light chains are express at the same rate and assemble in a similar manner, the ratio for the three molecules should be 25% IgGκ, 25% IgGλ, and 50% IgGκλ. However, an unbalanced expression level of the two chains is sometimes observed, leading a decrease in bispecific yield. One solution could be to increase the expression of the less expressed chain to restore the balance. However, this approach has been unsuccessful (as shown in the working examples provided herein).

In contrast, the methods of the disclosure are effective in limiting the expression of the dominant chain and, thus, equilibrating their relative abundance. The methods disclosed herein lead to a significant increase in productivity and final bispecific yields both in transient expression systems as well as in stably transfected CHO cells. Thus, the reduction of the expression of one or several polypeptides can lead to an overall increase in productivity. While the examples provided herein use κλ-bodies, the methods disclosed herein are applicable to other bispecific antibody formats and any other protein complex composed of several different polypeptides.

In some embodiments, the disclosure provides methods to increase the production yield of a protein complex composed of several polypeptides by decreasing the expression rate of one or several of the polypeptides. In some embodiments, the reduction in expression of one of the polypeptides is achieved by modification of transcription rate, translation rate, or mRNA stability. In some embodiments, the reduction in expression rate of one of the polypeptides is achieved by the modifying the mRNA secondary structure. In some embodiments, the reduction in expression of one of the polypeptides is achieved by modifying transcription rate, modifying translation rate, modifying mRNA stability, modifying mRNA secondary structure or by a combination of any of these factors.

In some embodiments, the reduction in expression of one of the polypeptides in the protein complex is achieved by modifying translation rate. In some embodiments, the reduction in expression of one of the polypeptides in the protein complex is achieved by altering the codon composition of that polypeptide. In some embodiments, the reduction in expression of one of the polypeptides in the protein complex is achieved by modifying translation rate and altering the codon composition of that polypeptide.

In some embodiments, the reduction in expression of one of the polypeptides in the protein complex is achieved by modifying translation rate. In some embodiments, the reduction in expression of one of the polypeptides in the protein complex is achieved by altering the codon composition of that polypeptide via the replacement of certain codons with codons that are less frequently used in the host cell that is used for expression of the protein complex. In some embodiments, the reduction in expression of one of the polypeptides in the protein complex is achieved by modifying translation rate, and altering the codon composition of that polypeptide via the replacement of certain codons with codons that are less frequently used in the host cell that is used for expression of the protein complex.

In some embodiments, the reduction in expression of one of the polypeptides in the protein complex is achieved by modifying translation rate. In some embodiments, the reduction in expression of one of the polypeptides in the protein complex is achieved by altering the codon composition of that polypeptide via the replacement of certain codons with codons that are less frequently used in a mammalian host cell used for expression of the protein complex. In some embodiments, the reduction in expression of one of the polypeptides in the protein complex is achieved by modifying translation rate and altering the codon composition of that polypeptide via the replacement of certain codons with codons that are less frequently used in a mammalian host cell used for expression of the protein complex.

In some embodiments, the protein complex is a multispecific antibody. In some embodiments, the protein complex is a bispecific antibody. In some embodiments, the bispecific antibody is a composed of two different light chains and a common heavy chain.

In some embodiments, the bispecific antibody includes a human lambda light chain and a human kappa light chain.

In some embodiments, the bispecific antibody includes a first and the second antigen-binding regions each comprise at least one complementarity determining region (CDR). In some embodiments, the first and the second antigen-binding regions each comprise at least two CDRs. In some embodiments, the first and the second antigen-binding regions each comprise each comprise three CDRs. In some embodiments, the CDRs are from an immunoglobulin heavy chain. In some embodiments, the heavy chain is a human heavy chain. In some embodiments, the CDRs are from a lambda light chain. In some embodiments, the CDRs are from a kappa light chain.

In some embodiments, the first antigen-binding region comprises a first immunoglobulin heavy chain variable domain, and the second antigen-binding region comprises a second immunoglobulin heavy chain variable domain.

In some embodiments, the first and the second immunoglobulin heavy chain variable domains independently comprise a human CDR, a mouse CDR, a rat CDR, a rabbit CDR, a monkey CDR, an ape CDR, a synthetic CDR, and/or a humanized CDR. In some embodiments, the CDR is human and is somatically mutated.

In some embodiments, the bispecific antibodies comprise a human framework region (FR). In some embodiments, the human FR is a somatically mutated human FR.

In some embodiments, the bispecific antibodies are obtained by screening a phage library comprising antibody variable regions for reactivity toward an antigen of interest.

In some embodiments, the first and/or the second antigen-binding regions of the bispecific antibodies are obtained by immunizing a non-human animal such as a mouse, a rat, a rabbit, a monkey, or an ape with an antigen of interest and identifying an antibody variable region nucleic acid sequence encoding variable region specific for the antigen of interest.

In some embodiments, the bispecific antibody is a fully human bispecific antibody and has an affinity for each epitope, independently, in the micromolar, nanomolar, or picomolar range.

In some embodiments, the bispecific antibody is non-immunogenic or substantially non-immunogenic in a human. In some embodiments, the bispecific antibody lacks a non-native human T-cell epitope. In some embodiments, the modification of the CH1 region is non-immunogenic or substantially non-immunogenic in a human.

In some embodiments, the antigen-binding protein comprises a heavy chain, wherein the heavy chain is non-immunogenic or substantially non-immunogenic in a human.

In some embodiments, the heavy chain has an amino acid sequence that does not contain a non-native T-cell epitope. In some embodiments, the heavy chain comprises an amino acid sequence whose proteolysis cannot form an amino acid sequence of about 9 amino acids that is immunogenic in a human. In a specific embodiment, the human is a human being treated with the antigen-binding protein. In some embodiments, the heavy chain comprises an amino acid sequence whose proteolysis cannot form an amino acid sequence of about 13 to about 17 amino acids that is immunogenic in a human. In a specific embodiment, the human is a human being treated with the antigen-binding protein.

In some embodiments, more than one protein complex is co-expressed. In some embodiments, more than one antibody is co-expressed.

DETAILED DESCRIPTION

Figure 1:
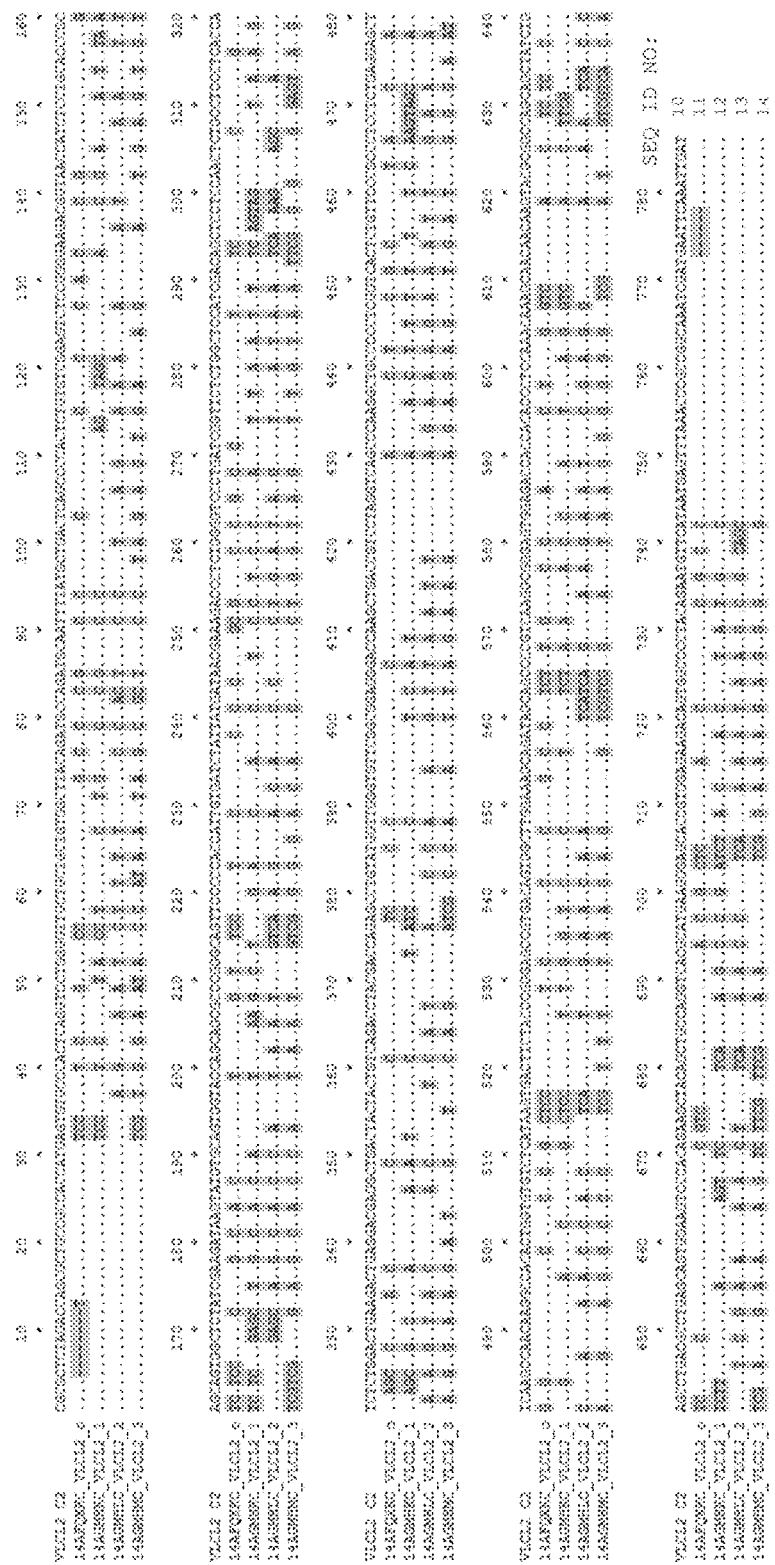
FIG. 1 is an illustration depicting the mutations introduced in the lambda light chain to modulate its expression. VLCL2, wild type sequence; VLCL2_0, optimized sequence; VLCL2_1, VLCL2_2, VLCL2_3, sequences with increased levels of deoptimization. The polynucleotide sequences (from top to bottom) correspond to SEQ ID NOs: 5-9, respectively, as shown in Table 1.3.

Recombinant expression in bacterial, yeast, insect, plant or mammalian cells is fundamental for the production of proteins that are used for research as well as therapeutic applications. Recently, the yield of recombinant protein expression in Chinese Hamster Ovary cells has been significantly enhanced by optimizing multiple parameters such as culture medium composition, fermentation parameters, as well as optimization of the constructs that are used to drive the expression of the gene encoding the recombinant protein of interest. These include the improvements at transcriptional and translational levels as well as mRNA secondary structures and stability. Another important element is the optimization of codon usages so that it matches the expression host and avoid limitation due to low abundance tRNAs. The optimization process also can also include the removal of sequence repeats, killer motifs and splice sites and stable RNA secondary structures are avoided. The codon usage and GC content can be simultaneously adapted for the expression in CHO cells or other host cells. The aim of such modifications is to maximize translation and stability of RNA so that translation and thus expression of the desired polypeptide is maximal.

Some proteins are composed of several polypeptides that can associate in complexes that can be covalently or non-covalently linked. Antibodies are an example of such a class of proteins as they are composed of four polypeptides (i.e. two heavy chains and two light chains) that are linked by disulfide bonds. Antibodies carry a unique specificity for a target antigen that is driven by the Fab portion while they can engage with the immune via their Fc portion. A number of currently used biological therapeutics for cancer are monoclonal antibodies directed against antigens that are over expressed by targeted cancer cells. When such antibodies bind to the tumor cells, several processes can be triggered such as antibody-dependent cellular toxicity (ADCC), antibody-dependent cellular phagocytosis or complement-dependent cytotoxicity (CDC). Due to their commercial and therapeutic importance, the expression of antibodies in CHO cells has been the subject of intense efforts of optimization, aiming at maximizing the expression of the two chains that compose the antibody. However, major differences can be observed as the levels of expression can vary up to 200-fold between antibodies. The expression level is determined by a several factors including the level of light chain synthesis and heavy and light chain compatibility for assembly. It appears that high expression of light chain is beneficial for the overall secretion rates of whole antibody (Strutzenberger et al., Changes during subclone development and ageing of human antibody-producing recombinant CHO cells, J. Biotechnol., vol. 69(2-3): 215-16 (1999)). Indeed, reduction of light chain expression leads to accumulation of heavy chain in the endoplasmic reticulum and limits productivity.

Targeting or neutralizing a single protein with a monoclonal antibody is not always sufficient to achieve efficacy and this limits the therapeutic use of monoclonal antibodies. It is increasingly clear that in a number of diseases the neutralization of one component of a biological system is not sufficient provide a beneficial effect. Thus multispecific antibodies capable of engaging more than one antigen, e.g., bispecific antibodies, have been developed. A large number of bispecific antibody formats have been described and two bispecific antibodies have been approved so far while many others are currently in clinical trials (Kontermann R E, Brinkmann U., Bispecific antibodies, Drug Discover Today, (2015), available at dx.doi.org/10.1016/j.drudis.2015.02.2008). In many cases the bispecific antibody is composed of more than two polypeptides. The correct assembly can be based on random pairing of the chains, leading to a mixture of molecules from which the bispecific antibody can be purified. Alternatively, the interface of the chains can be engineered so that the desired pairing can be preferably obtained. In any case, the co-expression of multiple chains implies a higher complexity and the relative expression rates and thus abundance of the chains composing the bispecific molecule can potentially have a major impact on overall yield and efficiency in assembly.

Previous optimization approaches aimed at increasing the expression levels of polypeptides in order to achieve higher production yields. In the case of protein complexes composed of multiple polypeptides, unbalanced expression can limit assembly of the desired molecule, promote production of unwanted products and limit the overall production yield.

The methods of the disclosure improve the expression of protein complexes by tuning the expression levels of each component required for the assembly of the complex. The methods of the disclosure are effective in limiting the expression of the dominant chain and, thus, equilibrating their relative abundance. The methods disclosed herein lead to a significant increase in productivity and final bispecific yields both in transient expression systems as well as in stably transfected CHO cells. Thus, the reduction of the expression of one or several polypeptides can lead to an overall increase in productivity.

Table 1 is a table depicting the constructs generated with different sequence optimization and deoptimization levels.

TABLE 1

| Clone | VKCK | VHCH | VLCL | |
|---|---|---|---|---|
| 44 | WT | WT | WT | |
| 15 | OPT | OPT | OPT | |
| 17 | OPT | OPT | WT | |
| 3 | OPT | OPT | Deopt_1 | |
| 13 | OPT | OPT | Deopt_2 | Deoptimization level |
| 19 | OPT | OPT | Deopt_3 | |

The sequences used are shown below in Tables 1.1, 1.2, and 1.3.

TABLE 1.1

VHCH WT (SEQ ID NO: 1) and VHCH OPT (SEQ ID NO: 2) sequences

VHCH      1  ATGGAATGGAGCTGGGTCTTTCTCTTCTTCCTGTCAGTAACTACAGGTGT

VHCH OPT  1  ATGGAATGGTCCTGGGTGTTCCTGTTCTTCCTGTCCGTGACCACCGGCGT

VHCH     51  CCACTCCGAGGTGCAGCTGTTGGAGTCTGGGGGAGGCTTGGTACAGCCTG

TABLE 1.1-continued

VHCH WT (SEQ ID NO: 1) and VHCH OPT (SEQ ID NO: 2) sequences

```
VHCH OPT     51 CCACTCCGAGGTGCAGCTGCTGGAATCTGGCGGCGGACTGGTCCAGCCTG

VHCH        101 GGGGGTCCCTGAGACTCTCCTGTGCAGCCTCTGGATTCACCTTTAGCAGC

VHCH OPT    101 GAGGCTCCCTGAGACTGTCTTGCGCCGCCTCCGGCTTCACCTTCTCCAGC

VHCH        151 TATGCCATGAGCTGGGTCCGCCAGGCTCCAGGGAAGGGGCTGGAGTGGGT

VHCH OPT    151 TACGCCATGTCCTGGGTGCGACAGGCCCTGGCAAGGGACTGGAATGGGT

VHCH        201 CTCAGCTATTAGTGGTAGTGGTGGTAGCACATACTACGCAGACTCCGTGA

VHCH OPT    201 GTCCGCCATCTCCGGCTCCGGCGGCTCTACCTACTACGCCGACTCCGTGA

VHCH        251 AGGGCCGGTTCACCATCTCCAGAGACAATTCCAAGAACACGCTGTATCTG

VHCH OPT    251 AGGGCCGGTTCACCATCTCCCGGGACAACTCCAAGAACACCCTGTACCTG

VHCH        301 CAAATGAACAGCCTGAGAGCCGAGGACACGGCCGTATATTACTGTGCGAA

VHCH OPT    301 CAGATGAACTCCCTGCGGGCCGAGGACACCGCCGTGTACTACTGCGCCAA

VHCH        351 AAGTTATGGTGCTTTTGACTACTGGGGCCAGGGAACCCTGGTCACAGTCT

VHCH OPT    351 GTCCTACGGCGCCTTCGACTACTGGGGCCAGGGCACCCTGGTGACAGTGT

VHCH        401 CGAGCGCCTCCACCAAGGGCCCATCGGTCTTCCCCCTGGCACCCTCCTCC

VHCH OPT    401 CCTCCGCCTCCACCAAGGGCCCATCCGTGTTCCCTCTGGCCCCCTTCCAGC

VHCH        451 AAGAGCACCTCTGGGGGCACAGCGGCCCTGGGCTGCCTGGTCAAGGACTA

VHCH OPT    451 AAGTCCACCTCTGGCGGAACCGCTGCCCTGGGCTGCCTGGTGAAAGACTA

VHCH        501 CTTCCCCGAACCGGTGACAGTCTCGTGGAACTCAGGAGCCCTGACCAGCG

VHCH OPT    501 CTTCCCCGAGCCCGTGACCGTGTCCTGGAACTCTGGCGCCCTGACCAGCG

VHCH        551 GCGTGCACACCTTCCCGGCTGTCCTACAGTCCTCAGGACTCTACTCCCTC

VHCH OPT    551 GAGTGCACACCTTCCCTGCCGTGCTGCAGTCCTCCGGCCTGTACTCCCTG

VHCH        601 AGCAGCGTGGTGACTGTGCCCTCCAGCAGCTTGGGCACCCAGACCTACAT

VHCH OPT    601 TCCTCCGTGGTGACCGTGCCCTCCAGCTCTCTGGGCACCCAGACCTACAT

VHCH        651 CTGCAACGTGAATCACAAGCCCAGCAACACCAAGGTGGACAAGAGAGTTG

VHCH OPT    651 CTGCAACGTGAACCACAAGCCCTCCAACACCAAGGTGGACAAGCGGGTGG

VHCH        701 AGCCCAAATCTTGTGACAAAACTCACACATGCCCACCGTGCCCAGCACCT

VHCH OPT    701 AACCCAAGTCCTGCGACAAGACCCACACCTGTCCTCCCTGCCCTGCCCCT

VHCH        751 GAACTCCTGGGGGGACCGTCAGTCTTCCTCTTCCCCCCAAAACCCAAGGA

VHCH OPT    751 GAACTGCTGGGCGGACCCTCCGTGTTTCTGTTCCCCCCAAAGCCCAAGGA

VHCH        801 CACCCTCATGATCTCCCGGACCCCTGAGGTCACATGCGTGGTGGTGGACG

VHCH OPT    801 CACCCTGATGATCTCCCGGACCCCCGAAGTGACCTGCGTGGTGGTGGACG

VHCH        851 TGAGCCACGAAGACCCTGAGGTCAAGTTCAACTGGTACGTGGACGGCGTG

VHCH OPT    851 TGTCCCACGAGGACCCTGAAGTGAAGTTCAATTGGTACGTGGACGGCGTG

VHCH        901 GAGGTGCATAATGCCAAGACAAAGCCGCGGGAGGAGCAGTACAACAGCAC

VHCH OPT    901 GAAGTGCACAACGCCAAGACCAAGCCCAGAGAGGAACAGTACAACTCCAC

VHCH        951 GTACCGTGTGGTCAGCGTCCTCACCGTCCTGCACCAGGACTGGCTGAATG

VHCH OPT    951 CTATCGGGTGGTGTCTGTGCTGACCGTGCTGCACCAGGACTGGCTGAACG

VHCH       1001 GCAAGGAGTACAAGTGCAAGGTCTCCAACAAAGCCCTCCCAGCCCCCATC

VHCH OPT   1001 GCAAAGAGTACAAGTGCAAGGTCTCCAACAAGGCCCTGCCTGCCCCCATC
```

TABLE 1.1-continued

VHCH WT (SEQ ID NO: 1) and VHCH OPT (SEQ ID NO: 2) sequences

```
VHCH     1051 GAGAAAACCATCTCCAAAGCCAAAGGGCAGCCCCGAGAACCACAGGTGTA

VHCH OPT 1051 GAAAAGACCATCTCCAAGGCCAAGGGCCAGCCCCGCGAACCCCAGGTCTA

VHCH     1101 TACCCTGCCCCCATCTCGGGAGGAGATGACCAAGAACCAGGTCAGCCTGA

VHCH OPT 1101 CACACTGCCACCTAGCCGGGAAGAGATGACCAAGAACCAGGTGTCCCTGA

VHCH     1151 CTTGCCTGGTCAAAGGCTTCTATCCCAGCGACATCGCCGTGGAGTGGGAG

VHCH OPT 1151 CCTGTCTGGTGAAAGGCTTCTACCCCTCCGATATCGCCGTGGAATGGGAG

VHCH     1201 AGCAACGGGCAGCCGGAGAACAACTACAAGACCACGCCTCCCGTGCTGGA

VHCH OPT 1201 TCCAACGGCCAGCCCGAGAACAACTACAAGACCACCCCCCCTGTGCTGGA

VHCH     1251 CTCCGACGGCTCCTTCTTCCTCTATAGCAAGCTCACCGTGGACAAGTCCA

VHCH OPT 1251 CTCCGACGGCTCATTCTTCCTGTACTCCAAGCTGACCGTGGACAAGTCCC

VHCH     1301 GGTGGCAGCAGGGGAACGTCTTCTCATGCTCCGTGATGCATGAGGCTCTG

VHCH OPT 1301 GGTGGCAGCAGGGCAACGTGTTCTCCTGCAGCGTGATGCACGAGGCCCTG

VHCH     1351 CACAACCACTACACGCAGAAGAGCCTCTCCCTGTCTCCGGGTTAA
              (SEQ ID NO: 1)

VHCH OPT 1351 CACAACCACTACACCCAGAAGTCCCTGTCCCTGAGCCCCGGCTAA
              (SEQ ID NO: 2)
```

TABLE 1.2

VKCK WT (SEQ ID NO: 3) and VKCK OPT (SEQ ID NO: 4) sequences

```
VKCK     1   ATGAGTGTGCCCACTCAGGTCCTGGGGTTGCTGCT
             GCTGTGGCTTACAGATGCCAGATGTGACATCCAGA

VKCK OPT 1   ATGTCCGTGCCCACCCAGGTGCTGGGACTGCTGCT
             GCTGTGGCTGACCGACGCCAGATGCGACATCCAGA

VKCK     71  TGACCCAGTCTCCATCCTCCCTGTCTGCATCTGTA
             GGAGACAGAGTCACCATCACTTGCCAGGCGAGTCA

VKCK OPT 71  TGACCCAGAGCCCTTCCAGCCTGAGCGCCTCCGTG
             GGCGACAGAGTGACCATCACCTGTCAGGCCTCCCA

VKCK     141 GTCCATTAGTAGTTATTTAAATTGGTATCAGCAGA
             AACCAGGGAAAGCCCCTAAGCTCCTGATCTACGCT

VKCK OPT 141 GTCCATCTCCTCCTACCTGAACTGGTATCAGCAGA
             AGCCCGGCAAGGCCCCTAAGCTGCTGATCTACGCC

VKCK     211 GCATCCTCGTTGGAAACAGGGGTCCCATCAAGGTT
             CAGTGGAAGTGGATCTGGGACAGATTTTACTTTCA

VKCK OPT 211 GCCTCCTCCCTGGAAACCGGCGTGCCCTCCAGATT
             CTCCGGCTCCGGCTCTGGCACCGACTTCACCTTCA

VKCK     281 CCATCAGCAGCCTGCAGCCTGAAGATATTGCAACA
             TATTACTGTCAGCAGAAGCACCCCCGGGGGCCGAG

VKCK OPT 281 CCATCTCCAGCCTGCAGCCCGAGGATATCGCCACC
             TACTACTGCCAGCAGAAGCACCCTCGGGGCCCTAG

VKCK     351 GACCTTCGGCCAAGGGACCAAGGTGGAAATCAAAC
             GTACGGTGGCTGCACCATCTGTCTTCATCTTCCCG

VKCK     351 AACCTTCGGCCAGGGCACCAAGGTGGAAATCAAGC
OPT          GGACCGTGGCCGCTCCCTCCGTGTTCATCTTCCCA

VKCK     421 CCATCTGATGAGCAGTTGAAATCTGGAACTGCCTC
             TGTTGTGTGCCTGCTGAATAACTTCTATCCCAGAG

VKCK     421 CCCTCCGACGAGCAGCTGAAGTCCGGCACCGCCAG
OPT          CGTCGTGTGCCTGCTGAACAACTTCTACCCACACGCG

VKCK     491 AGGCCAAAGTACAGTGGAAGGTGGATAACGCCCTC
             CAATCGGGTAACTCCCAGGAGAGTGTCACAGAGCA

VKCK     491 AGGCCAAGGTGCAGTGGAAGGTGGACAACGCCCTG
OPT          CAGTCCGGCAACTCCCAGGAATCCGTCACCGAGCA

VKCK     561 GGACAGCAAGGACAGCACCTACAGCCTCAGGAGCA
             CCCTGACGCTGAGCAAAGCAGACTACGAGAAACAC

VKCK     561 GGACTCCAAGGACAGCACCTACTCCCTGTCCTCCA
OPT          CCCTGACCCTGTCCAAGGCCGACTACGAGAAGCAC

VKCK     631 AAAGTCTACGCCTGCGAAGTCACCCATCAGGGCCT
             GAGCTGCCCGTCCAAAGACTACGGGAGAACAGAAG

VKCK     631 AAGGTGTACGCCTGCGAAGTGACCCACCAGGGCCT
OPT          GTCCAGCCCCGTGACCAAGTCCTTCAACCGGGGCG

VKCK     701 AGTGTTAA (SEQ ID NO: 3)

VKCK     701 AGTGCTAA (SEQ ID NO: 4)
OPT
```

TABLE 1.3

```
VLCL2    1   ATGAGTGTGCCCACTCAGGTCCTGGGGTTGCTGCTGCTGTGGCTTACAGATGCCAGAT
             GCAATTTTATGCTGACTCAGCCCCACTCTGTG
```

TABLE 1.3-continued

| | | |
|---|---|---|
| VLCL2OPT | 1 | ATGTCCGTGCCTACCCAGGTGCTGGGCCTGCTGCTGCTGTGGCTGACCGACGCCCGGT GCAACTTCATGCTGACCCAGCCCCACTCCGTG |
| VLCL2DEOPT_1 | 1 | ATGTCCGTGCCTACCCAGGTCTTAGGCCTTCTGCTGCTCTGGTTGACAGACGCCCGGT GCAACTTCATGCTGACTCAGCCCCACAGTGTT |
| VLCL2DEOPT_2 | 1 | ATGAGTGTACCGACTCAAGTACTTGGGCTTCTTCTTCTTTGGCTTACCGACGCACGTT GCAACTTCATGCTTACTCAACCGCACTCAGTA |
| VLCL2DEOPT_3 | 1 | ATGTCGGTTCCGACGCAAGTATTAGGGCTCCTATTACTATGGTTAACGGACGCGCGTT GCAACTTCATGTTAACGCAACCGCATTCGGTA |
| VLCL2 | 91 | TCGGAGTCTCCGGGGAAGACGGTAACCATCTCCTGCACCCGCAGCAGTGGCTCTATCG AAGATAAGTATGTGCAGTGGTACCAGCAGCGC |
| VLCL2OPT. | 91 | TCCGAGTCCCCAGGCAAGACCGTGACCATCTCCTGCACCCGGTCCTCCGGCTCCATCG AGGACAAATACGTGCAGTGGTATCAGCAGCGG |
| VLCL2DEOPT_1 | 91 | AGCGAGTCTCCGGGAAAGACCGTGACAATCTCATGTACTAGATCCTCTGGGAGCATTG AGGACAAATACGTACAGTGGTATCAGCAAAGG |
| VLCL2DEOPT_2 | 91 | TCAGAGTCACCGGGGAAAACTGTAACCATATCATGCACTCGTAGCAGTGGGAGCATAG AGGACAAATACGTCCAATGGTATCAACAACGT |
| VLCL2DEOPT_3 | 91 | TCGGAATCGCCGGGGAAAACGGTTACGATATCGTGTACGCGTTCGTCGGGCTCGATAG AGGACAAATACGTCCAATGGTATCAACAACGT |
| VLCL2 | 181 | CCGGGCAGTTCCCCCACCATTGTGATCTATTATGATAACGAAAGACCCTCTGGGGTCC CTGATCGGTTCTCTGGCTCCATCGACAGCTCC |
| VLCL2 OPT. | 181 | CCTGGCTCCTCCCCTACCATCGTGATCTACTACGACAACGAGCGGCCCTCCGGCGTGC CCGACCGGTTCTCTGGCTCTATCGACTCCTCC |
| VLCL2DEOPT_1 | 181 | CCCGGTAGTTCGCCAACCATCGTGATATATTACGATAATGAACGCCCTTCCGGCGTCC CAGATCGTTTTTCAGGATCTATTGACTCCAGT |
| VLCL2DEOPT_2 | 181 | CCGGGGTCATCACCGACCATAGTCATATATTACGACAACGAACGTCCGTCAGGTGTAC CGGATCGTTTCTCAGGTTCAATAGACTCATCA |
| VLCL2DEOPT_3 | 181 | CCGGGGTCGTCGCCGACGATAGTCATATATTACGATAACGAACGTCCGTCGGGTGTAC CGGATCGTTTTTCGGGTTCAATAGATTCGTCG |
| VLCL2 | 271 | TCCAACTCTGCCTCCCTCACCATCTCTGGACTGAAGACTGAGGACGAGGCTGACTACT ACTGTCAGACCTACGACCAGACGGTGTATGGT |
| VLCL2OPT. | 271 | TCCAACTCCGCCTCCCTGACCATCAGCGGCCTGAAAACCGAGGACGAGGCCGACTACT ACTGCCAGACCTACGACCAGTCCCTGTACGGC |
| VLCL2DEOPT_1 | 271 | AGCAACTCTGCTTCACTAACGATCAGCGGGCTCAAGACAGAGGACGAAGCAGATTACT ACTGCCAGACCTACGATCAATCCCTGTATGGC |
| VLCL2DEOPT_2 | 271 | AGCAACAGCGCCTCACTCACCATATCAGGGCTTAAAACCGAGGACGAAGCCGACTACT ATTGCCAAACTTACGACCAAAGCCTCTACGGA |
| VLCL2DEOPT_3 | 271 | TCGAACTCGGCGAGTCTAACGATATCGGGGCTAAAAACGGAAGATGAGGCGGACTATT ACTGCCAAACGTACGACCAATCGCTCTACGGA |
| VLCL2 | 361 | TGGGTGTTCGGCGGAGGGACCAAGCTGACCGTCCTAGGTCAGCCCAAGGCTGCCCCCT CGGTCACTCTGTTCCCGCCCTCCTCTGAGGAG |
| VLCL2OPT. | 361 | TGGGTGTTCGGCGGAGGCACCAAGCTGACCGTCCTAGGTCAACCCAAGGCCGCTCCCT CCGTGACCCTGTTCCCTCCATCCTCCGAGGAA |
| VLCL2DEOPT_1 | 361 | TGGGTGTTCGGTGGCGGAACTAAGCTGACCGTCCTAGGTCAACCCAAAGCCGCTCCTT CTGTTACTTTGTTTCCCCCAAGTAGCGAGGAA |
| VLCL2DEOPT_2 | 361 | TGGGTATTCGGGGGTGGTACAAAACTTACTGTCCTAGGTCAACCGAAAGCAGCACCGT CAGTAACACTTTTTCCGCCGTCATCAGAGGAA |
| VLCL2DEOPT_3 | 361 | TGGGTATTCGGTGGTGGAACGAAACTAACGGTCCTAGGTCAACCGAAAGCGGCACCGT CGGTTACGCTATTTCCGCCGTCGTCGGAAGAA |
| VLCL2 | 451 | CTTCAAGCCAACAAGGCCACACTGGTGTGCTCATAAGTGACTTCTACCCGGGAGCCGT GACAGTGGCTTGGAAAGCAGATGAGCAGCCC |

TABLE 1.3-continued

```
VLCL2OPT.      451 CTGCAGGCCAACAAGGCCACCCTGGTCTGCCTGATCTCCGACTTCTACCCTGGCGCCG
                   TGACCGTGGCCTGGAAGGCCGACAGCTCTCCT

VLCL2DEOPT_1   451 CTTCAGGCCAACAAGGCAACACTCGTGTGTCTGATCTCCGACTTCTATCCTGGGCGG
                   TTACCGTGGCCTGGAAAGCTGATAGCTCTCCA

VLCL2DEOPT_2   451 CTCCAAGCAAACAAAGCAACCCTCGTATGCCTCATATCAGACTTCTATCCGGGGCAG
                   TAACCGTAGCATGGAAAGCAGATTCATCACCG

VLCL2DEOPT_3   451 TTACAAGCGAACAAAGCGACGCTCGTCTGCCTCATATCGGATTTTTATCCGGGTGCAG
                   TAACGGTAGCGTGGAAAGCGGATTCGTCGCCG

VLCL2         541 GTCAAGGCGGGAGTGGAGACCACCACACCCTCCAAACAAAGCAACAACAAGTACGCGG
                   CCAGCAGCTATCTGAGCCTGACGCCTGAGCAG

VLCL2OPT.      541 GTGAAGGCCGGCGTGGAAACCACCACCCCTTCCAAGCAGTCCAACAAACAAATACGCC
                   GCTCCTCCTACCTGTCCCTGACCCCTGAGCAG

VLCL2DEOPT_1   541 GTAAAGGCAGGCGTCGAGACAACCACTCCCTCAAAGCAGTCCAACAACAAATACGCCG
                   CTTCGAGCTATCTGTCTTTGACGCCTGAACAG

VLCL2DEOPT_2   541 GTCAAAGCAGGGGTAGAAACTACCACCCCGTCAAAGCAGAGCAACAACAAATACGCAG
                   CAAGCTCATACCTCAGCCTTACCCCGGAACAA

VLCL2DEOPT_3   541 GTCAAAGCGGGTGTAGAAACGACGACGCCGTCGAAGCAATCGAACAACAAATATGCGG
                   CGTCGTCATACCTATCGCTAACGCCGGAACAA

VLCL2         631 TGGAAGTCCCACAGAAGCTACAGCTGCCAGGTCACGCATGAAGGGAGCACCGTGGAGA
                   AGACAGTGGCCCCTACAGAATGTTCATAA

VLCL2OPT.      631 TGGAAGTCCCACCGGTCCTACAGCTGCCAGGTCACACACGAGGGCTCCACCGTGGAAA
                   AGACCGTGGCCCCTACCGAGTGCTCCTAA

VLCL2DEOPT_1   631 TGGAAGAGTCATCGAAGCTACTCATGCCAAGTGACCCACGAGGGATCTACAGTCGAGA
                   AAACCGTGGCTCCAACTGAGTGTTCCTAA

VLCL2DEOPT_2   631 TGGAAAATCACACCGTAGCTACTCATGCCAAGTAACCCACGAAGGGTCAACCGTAGAAA
                   AAACTGTAGCACCGACCGAGTGCAGCTAA

VLCL2DEOPT_3   631 TGGAAAATCGCATCGTTCGTATTCGTGCCAAGTAACGCATGAAGGGTCGACGGTAGAAA
                   AAACGGTAGCGCCGACGGAATGTTCGTAA
```

Sequences for VLCL2 WT (SEQ ID NO: 5, shown in row 1 of the alignment),
VLCL2 OPT (SEQ ID NO: 6, shown in row 2 of the alignment),
VLCL2 DEOPT_1 (SEQ ID NO: 7, shown in row 3 of the alignment),
VLCL2 DEOPT_2 (SEQ ID NO: 8, shown in row 4 of the alignment),
and VLCL2 DEOPT_3 (SEQ ID NO: 9, shown in row 5 of the alignment) sequences Table 2 is a table showing the following data for each construct: total IgG and bispecific antibody quantity after purification as well as the proportion of bispecific determined by HIC.

TABLE 2

| Clone | VKCK 5a3M3 | VHCH dummy | VLCL C2 | Total IgG Quantity (μg) | κλ-body™ Quantity (μg) | κλ-body™ % by HIC |
|---|---|---|---|---|---|---|
| 44 | WT | WT | WT | 1467 | 272 | 21.60 |
| 15 | OPT | OPT | OPT | 1160 | 120 | 14.43 |
| 17 | OPT | OPT | WT | 1430 | 292 | 29.41 |
| 3 | OPT | OPT | Deopt_1 | 1463 | 442 | 38.14 |
| 13 | OPT | OPT | Deopt_2 | 1458 | 444 | 42.93 |
| 19 | OPT | OPT | Deopt_3 | 1000 | 310 | 39.69 |

Table 3 depicts total IgG productivity, bispecific % by HIC after protein A purification, and the amount of purified bispecific from CHO cell culture supernatant for representative pools for each construct.

TABLE 3

| Name | Productivity (Total IgG in supernatant mg/mL) | HIC Bi % Post PA | Bi purified mg/mL of culture |
|---|---|---|---|
| 44 | 0.8 | 34.7 | 0.28 |
| 15 | 0.8 | 18.1 | 0.13 |
| 17 | 1.3 | 17.5 | 0.29 |
| 3 | 1.2 | 39.9 | 0.43 |
| 13 | 1.9 | 38.5 | 0.69 |
| 19- | 1.6 | 20.9 | 0.45 |

The polynucleotides and constructs thereof used in the methods provided herein can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, 2nd Ed, (1989) Cold Spring Harbor Press, Cold Spring Harbor, N.Y., and under current regulations described in United States Dept. of HHS, National Institute of Health (NIH) Guidelines for Recombinant DNA Research.

Also provided are constructs comprising the nucleic acids described herein inserted into a vector, where such constructs may be used for a number of different screening applications as described in greater detail below. In some embodiments, a single vector (e.g., a plasmid) will contain nucleic acid coding sequence for a single peptide display scaffold. In other embodiments, a single vector (e.g., a plasmid) will contain nucleic acid coding sequence for a two or more peptide display scaffolds.

Viral and non-viral vectors may be prepared and used, including plasmids, which provide for replication of biosensor-encoding DNA and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transformation and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the peptide display scaffolds. For expression, the gene product encoded by a polynucleotide of the disclosure is expressed in any convenient expression system, including, for example, bacterial, yeast, insect, amphibian and mammalian systems. Suitable vectors and host cells are described in U.S. Pat. No. 5,654,173. In the expression vector, a polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Eukaryotic promoters suitable for use include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad., Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters may be, furthermore, either constitutive or regulatable. Inducible elements are DNA sequence elements that act in conjunction with promoters and may bind either repressors e.g., lacO/LAC Iq repressor system in *E. coli*) or inducers (e.g., gall/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below.

Expression cassettes may be prepared comprising a transcription initiation region, the gene or fragment thereof, and a transcriptional termination region. After introduction of the DNA, the cells containing the construct may be selected by means of a selectable marker the cells expanded and then used for expression.

The above described expression systems may be employed with prokaryotes or eukaryotes in accordance with conventional ways, depending upon the purpose for expression. In some embodiments, a unicellular organism, such as *E. coli, B. subtilis, S. cerevisiae*, insect cells in combination with baculovirus vectors, or cells of a higher organism such as vertebrates, e.g., COS 7 cells, HEK 293, CHO, Xenopus Oocytes, etc., may be used as the expression host cells. In other situations, it is desirable to use eukaryotic cells, where the expressed protein will benefit from native folding and post-translational modifications.

Specific expression systems of interest include bacterial, yeast, insect cell and mammalian cell derived expression systems. Expression systems in bacteria include those described in Chang et al., Nature (1978) 275:615; Goeddel et al., Nature (1979) 281:544; Goeddel et al., Nucleic Acids Res. (1980) 8:4057; EP 0 036,776; U.S. Pat. No. 4,551,433; DeBoer et al., Proc. Natl. Acad. Sci. (USA) (1983) 80:21-25; and Siebenlist et al., Cell (1980) 20:269.

Mammalian expression is accomplished as described in Dijkema et al., EMBO J. (1985) 4:761, Gorman et al., Proc. Natl. Acad. Sci. (USA) (198) 79:6777, Boshart et al., Cell (1985) 41:521 and U.S. Pat. No. 4,399,216. Other features of mammalian expression are facilitated as described in Ham and Wallace, Meth. Enz. (1979) 58:44, Barnes and Sato, Anal. Biochem. (1980) 102:255, U.S. Pat. Nos. 4,767, 704, 4,657,866, 4,927,762, 4,560,655, WO 90/103430, WO 87/00195, and U.S. RE 30,985.

As will be appreciated by those in the art, the type of host cells suitable for use can vary widely. In some embodiments, the cell is a bacterial cell, a yeast cell or a mammalian cell. In some embodiments, the biological entity is a bacterial cell. In some embodiments, the bacterial cell is *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis*, or *Klebsiella pneumoniae*.

The constructs can be introduced into the host cell by any one of the standard means practiced by one with skill in the art to produce a cell line of the disclosure. The nucleic acid constructs can be delivered, for example, with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-

722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like.

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA and oligonucleotide synthesis, as well as tissue culture and transformation e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery and treatment of patients.

As utilized in accordance with the present disclosure, the following terms, unless otherwise indicated, shall be understood to have the following meanings:

The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term "polypeptide" is used herein as a generic term to refer to native protein, fragments, or mutants of a polypeptide sequence. Hence, native protein fragments, and mutants are species of the polypeptide genus. Preferred polypeptides in accordance with the disclosure comprise cytokines and antibodies.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and antibodies in an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule, Certain classes have subclasses as well, such as $IgG_1$, $IgG_2$, and others. Furthermore, in humans, the light chain may be a kappa chain or a lambda chain.

The term "fragments thereof" as used herein shall mean a segment of a polynucleotide sequence or polypeptide sequence that is less than the length of the entire sequence. Fragments as used herein comprised functional and nonfunctional regions. Fragments from different polynucleotide or polypeptide sequences are exchanged or combined to create a hybrid or "chimeric" molecule. Fragments are also used to modulate polypeptide binding characteristics to either polynucleotide sequences or to other polypeptides.

The term "promoter sequence" as used herein shall mean a polynucleotide sequence comprising a region of a gene at which initiation and rate of transcription are controlled. A promoter sequence comprises an RNA polymerase binding site as well as binding sites for other positive and negative regulatory elements. Positive regulatory elements promote the expression of the gene under control of the promoter sequence. Negative regulatory elements repress the express of the gene under control of the promoter sequence. Promoter sequences used herein are found either upstream or internal to the gene being regulated. Specifically, the term "first promoter sequence" versus "second promoter sequence" refers to the relative position of the promoter sequence within the expression vector. The first promoter sequence is upstream of the second promoter sequence.

The term "selection gene" as used herein shall mean a polynucleotide sequence encoding for a polypeptide that is necessary for the survival of the cell in the given culture conditions. If a cell has successfully incorporated the expression vector carrying the gene of interest, along with the selection gene, that cell will produce an element that will allow it to selectively survive under hostile culture conditions. "Selected" cells are those which survive under selective pressure and must have incorporated the expression vector. The term "selective pressure" as used herein shall mean the addition of an element to cell culture medium that inhibits the survival of cells not receiving the DNA composition.

The term "endogenous gene" as used herein shall mean a gene encompassed within the genomic sequence of a cell. The term "exogenous gene" as used herein shall mean a gene not encompassed within the genomic sequence of a cell. Exogenous genes are introduced into cells by the instant methods. The term "transgene" as used herein shall mean a gene that has been transferred from one organism to another.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end the lefthand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

Silent or conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

Silent or conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

A silent or conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

Other chemistry terms herein are used according to conventional usage in the art, as exemplified by The McGraw-Hill Dictionary of Chemical Terms (Parker, S., Ed., McGraw-Hill, San Francisco (1985)).

EXAMPLES

Example 1. Mutations Introduced in the Lambda Light Chain for Codon Optimization and Deoptimization in Mammalian Cells The anti-CD19×anti-CD47 bispecific antibody 44, which is based on the κλ-body technology, is composed by a common heavy chain and two different light chains. These chains are encoded by the plasmid construct 44 (Table 1). When this expression plasmid is transfected in mammalian cells, three molecules are produced by random assembly of the three chains: a monospecific IgGκ (containing two identical κ light chains), a monospecific IgGλ (containing two identical λ light chains), and a bispecific IgGκλ (containing one κ light chain and one λ light chain). If the two light chains are expressed at the same rate and assemble equally, the theoretical ratio for the three molecules should be 25% IgGκ, 25% IgGλ and 50% IgGκλ. In the case of the construct 44, there is a preferential expression of the λ light chains that leads to a suboptimal expression and yield of bispecific antibody. In order to improve this situation, optimization as well as deoptimization of the different chains has been performed to tune the relative ratios of the chains.

Codon optimization has been performed with the GeneOptimizer® software (GeneArt), on heavy, kappa and lambda chains. Different candidates were generated by cloning the optimized or not chains in the wild type plasmid of encoding the bispecific antibody 44.

Three different levels of codon deoptimization were performed on the lambda chain that is expressed in excess. Three constructs (3, 13 and 19 deoptimized lambda chain) were generated and combined with optimized heavy and kappa chains. Different degrees of deoptimization were applied to the λ light chain. Constructs 3, 13 Ind 19 contained increasingly deoptimized sequences (VLCL2-1, VLCL2-2 and VLCL2-3 respectively, see FIG. 1). Constructs 17 and 15 with an optimized lambda chain were also generated (Table 1).

Example 2. Cloning and Characterization of IgG Expressed in Peak Cells

Figure 2:
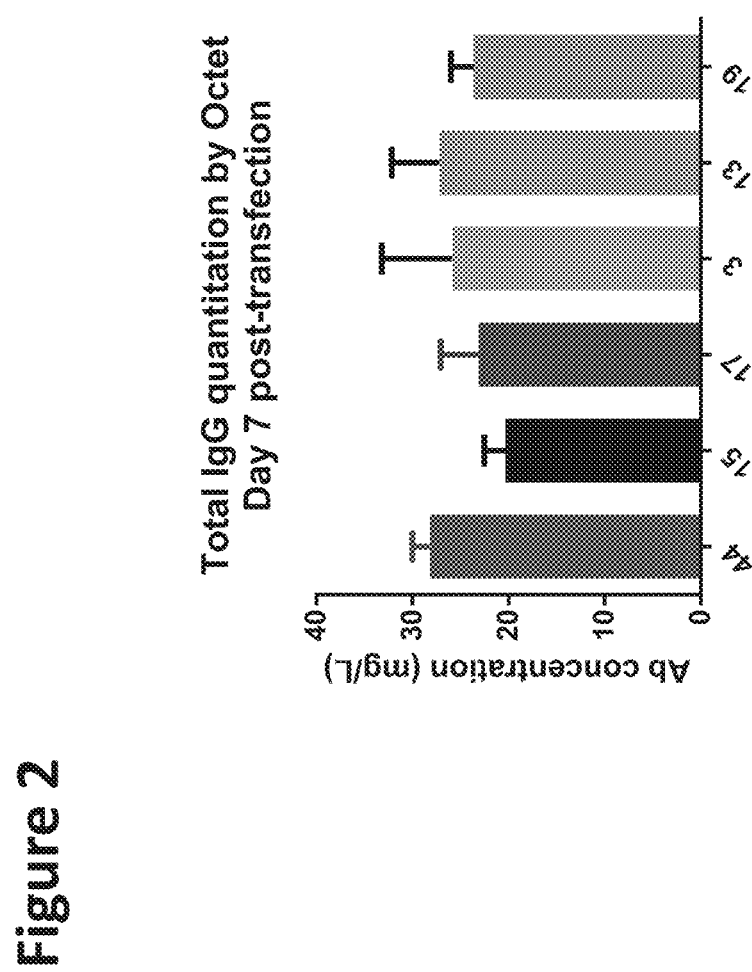
FIG. 2 is a graph indicating the concentration of IgG1 antibodies obtained in the supernatant of producing Peak cells measured using the OCTET technology.

The common heavy chain and two light chains (one kappa and one lambda) wild-type, optimized or deoptimized codon were cloned into a single mammalian expression pNOVI vector under three independent CMV promoters. After sequence verification, the IgG productivity for each construct was evaluated in Peak cells by two independent transient transfections using Lipofectamine 2000. Seven days after transfection, the total IgG expression was assessed by Octet technology. Except for the candidate 15, no major difference between the candidates in term of total IgG productivity was observed. A trend to a decrease in productivity was observed with construct 15 in which all chains had been optimized (FIG. 2). After 10 days of production in PEAK cells, total IgG were purified on Fc XL resin.

Figure 3A:
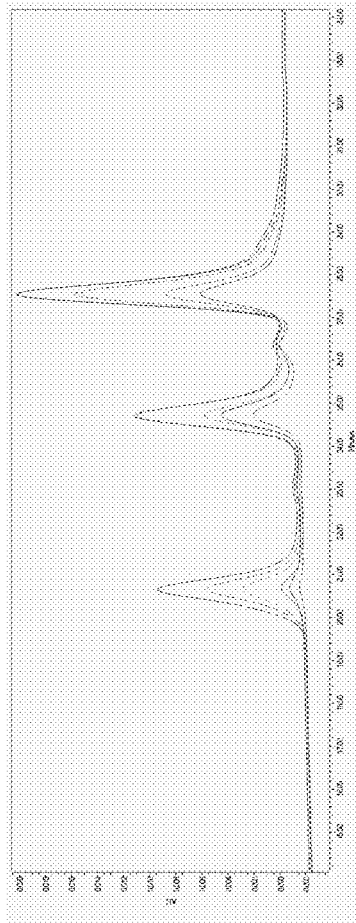
FIG. 3A is a graph of HIC profile of total purified IgG.
Figure 3B:
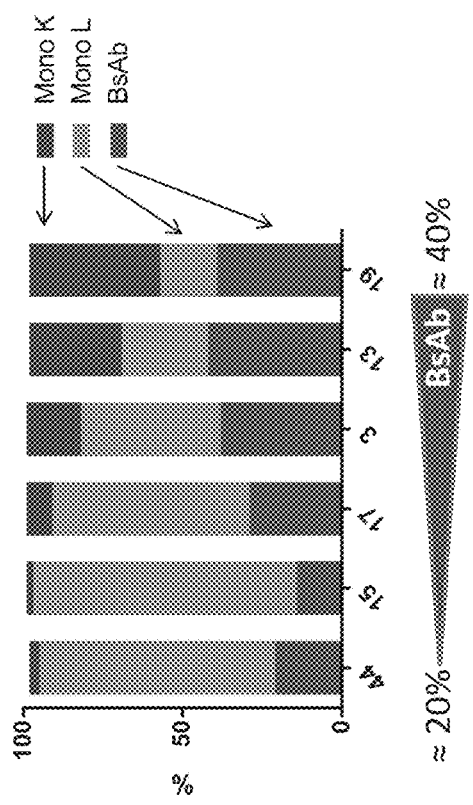
FIG. 3B is a graph showing the different percentage of monospecific kappa antibody, monospecific lambda antibody, and bispecific IgG for the different constructs and that were derived from the RIC profiles.

The distribution of the three different forms of IgG, monospecific lambda, monospecific kappa and bispecific antibody, was determined by HIC-HPLC analysis using ProPac HIC-10 column (Dionex) (FIG. 3A). A gradient of mobile phase A (0.001 M phosphate buffer+1 M ammonium sulphate, pH 3.5) from 85 to 35% and a growing gradient of mobile phase B (0.001 M phosphate buffer+acetonitrile 10%, pH 3.5) from 15% to 100% were applied. A blank was performed with mobile phase A, pH 7. The analysis of HIC area peak (FIG. 3B) shows a trend with increment of the percentage of bispecific for deoptimized candidates 3, 13 and 19 compared to wild-type 44 and optimized 15 and 17. The ratio of monospecific kappa and lambda for 3, 13 and 19 was significantly different compared to 44.

Figure 4:
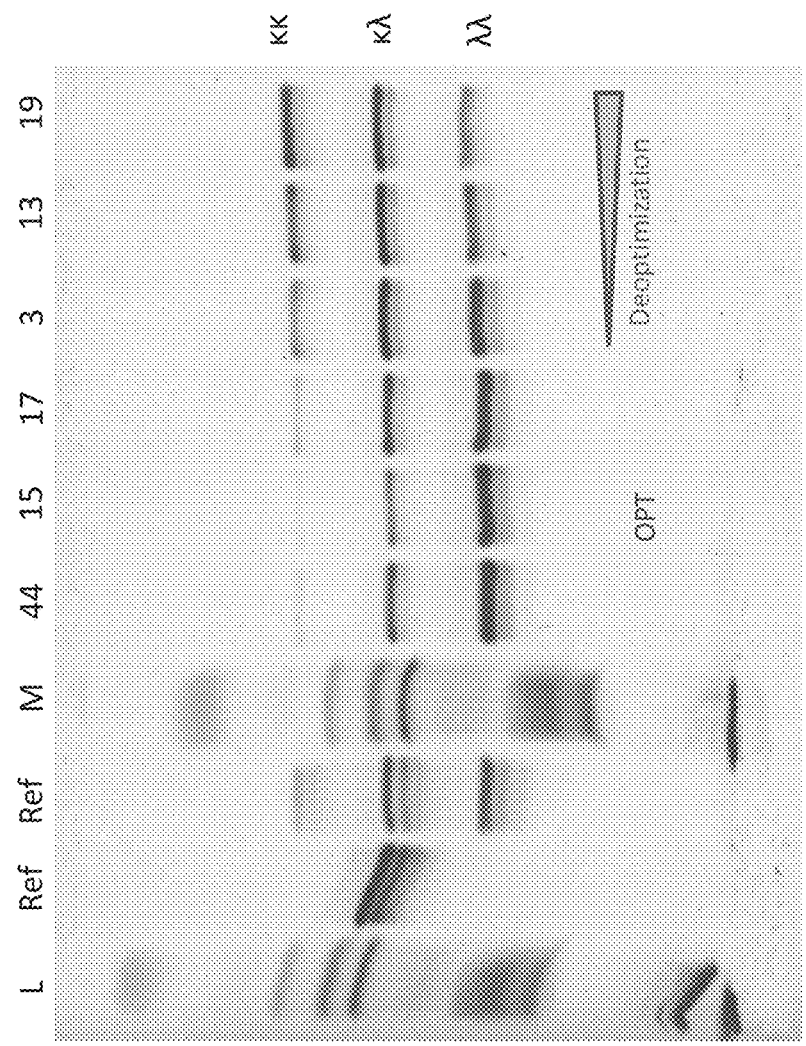
FIG. 4 is an isoelectric focusing polyacrylamide gel showing the expression of monoclonal and bispecific antibodies after affinity purification with CaptureSelect IgG Fc XL resin.

An IEF 7-11% was also performed to evaluate the distribution of total IgG (FIG. 4). Candidates with lambda optimization show an increment of monospecific lambda compared to clone 44 and less monospecific kappa and bispecific. Candidates 3, 13 and 19 showed a significant increase in monospecific kappa and bispecific.

Table 2 summarizes the data obtained for candidates expressed in PEAK cells. For the candidates 3, 13 and 19, the final percentage of bispecific obtained was higher, with an increase of the bispecific ratio from 21.6% for 44 to 42.9% for candidate 13. Interestingly, the highest codon deoptimization (construct 19) level of lambda chain increases the productivity of bispecific antibody.

Example 3. IgG Expression in Stably Transfected CHO Cells

Figure 5:
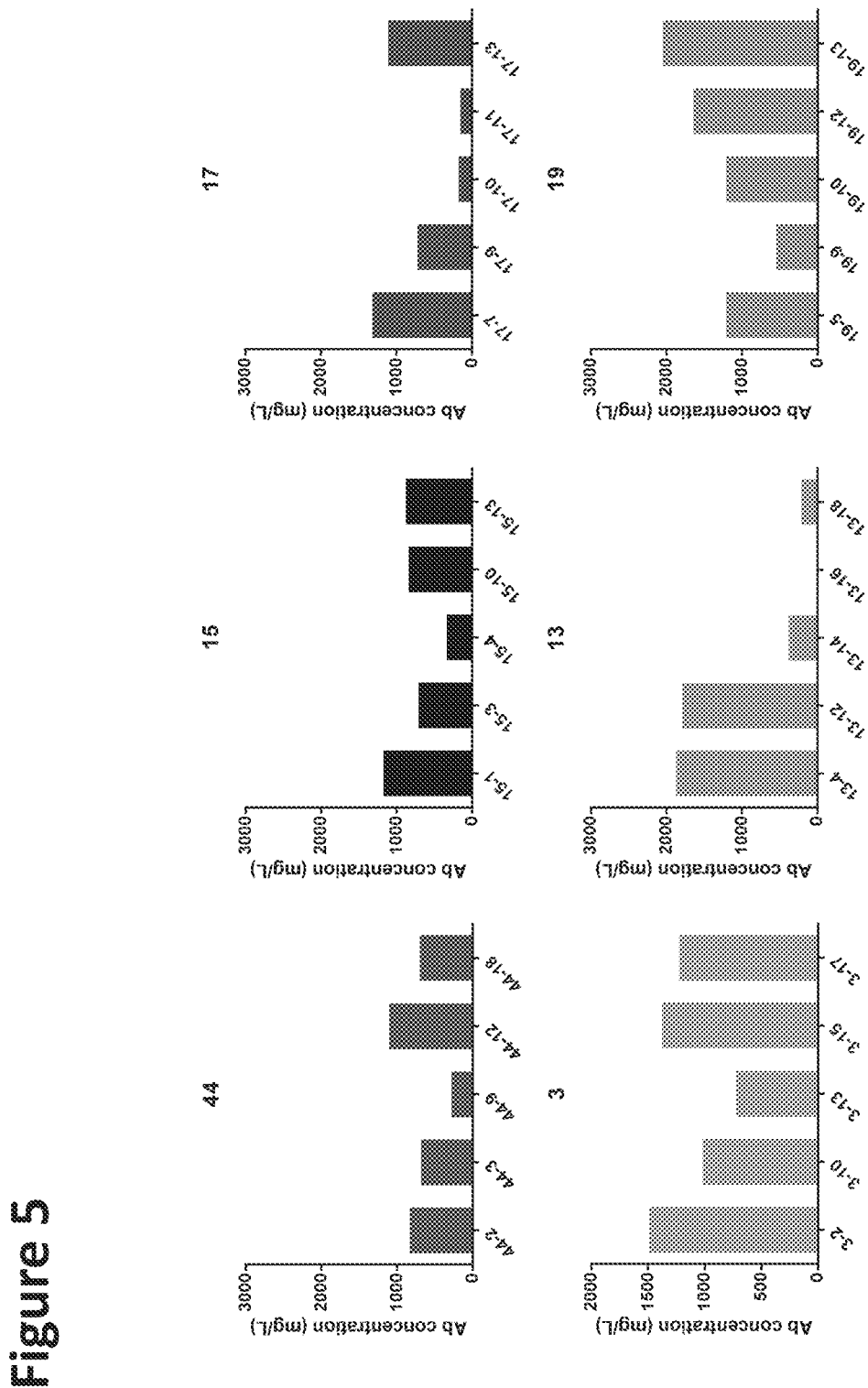
FIG. 5 is a series of graphs indicating the total IgG productivity for different constructs from several CHO cells pools.

After transfection by electroporation and selection with MSX, a screening by FACS was performed. The highest producing pools were selected for production in fed batch conditions. Total IgG productivity was assessed for different pools by Octet technology (FIG. 5). After purification by protein A, the ratio of the different chains was assessed by electrophoresis on an Agilent protein 80 chip monitoring the sizes of the heavy and light chains in reducing and denaturing condition.

Figure 6A:
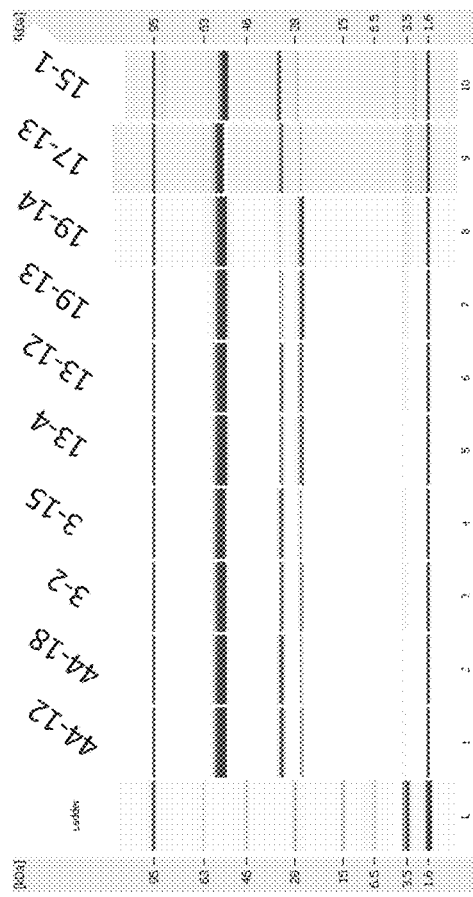
FIG. 6A is gel-like image representation of an Agilent protein 80 chip run monitoring the sizes of the heavy and light chains from purified IgG in reducing and denaturing conditions.
Figure 6B:
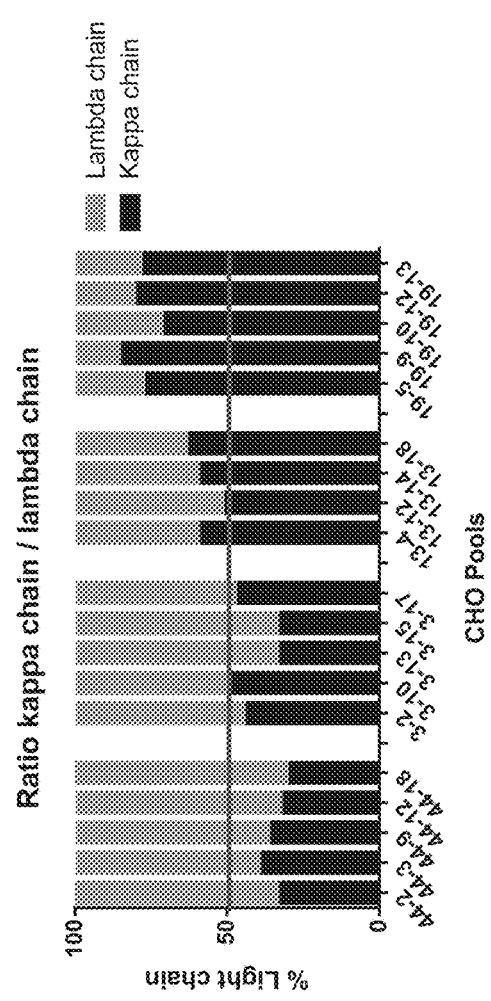
FIG. 6B is a graph showing the ratio of total kappa and lambda light chains for several CHO pools for each construct.
Figure 7:
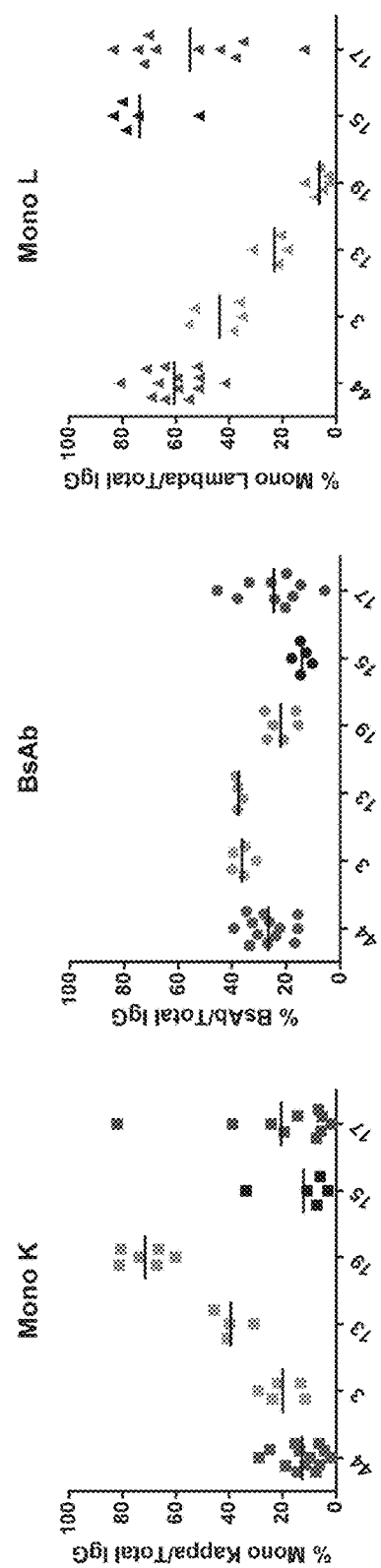
FIG. 7 is a series of graphs showing the distribution in % for mono Kappa, mono Lambda and bispecific antibodies expressed by several CHO cell pools.

As shown on Agilent analysis (FIG. 6A), for 44, the lambda chain was more represented than the kappa chain. For several CHO pools, the constructs 3 and 13 improved the equilibrium between the two light chains. With increased deoptimization of the lambda chain, the ratio was inversed when compared with the initial construct (44 versus 19). This was confirmed by calculating the ratio between the two light chains (FIG. 6B). Thus the balance between the two light chains, which was in favor of lambda chain for 44, was reversed gradually, correlating with the level of deoptimization. When all the productive pools are analyzed, a significant difference can be observed between the candidates 13, 19 and the candidate 44, with more kappa light chain and less lambda light chain. Based on these results, candidates 3 and 13 should show an increase in BsAb expression, as the two light chains are expressed at more equivalent levels After purification by protein A, the ratio of the different forms of IgG was assessed by HIC for all IgG producing pools (FIG. 7). The data shows that the level of monospecific lambda decreases gradually with the deoptimization level and the inverse pattern is observed for monospecific kappa. The bispecific levels reach a maximum of approximately 40% with a very homogenous distribution for the constructs 3 and 13. In contrast, the unbalanced expression of one of the two chains (as in 44 or 19) leads to a reduced level of bispecific production.

Figure 8:
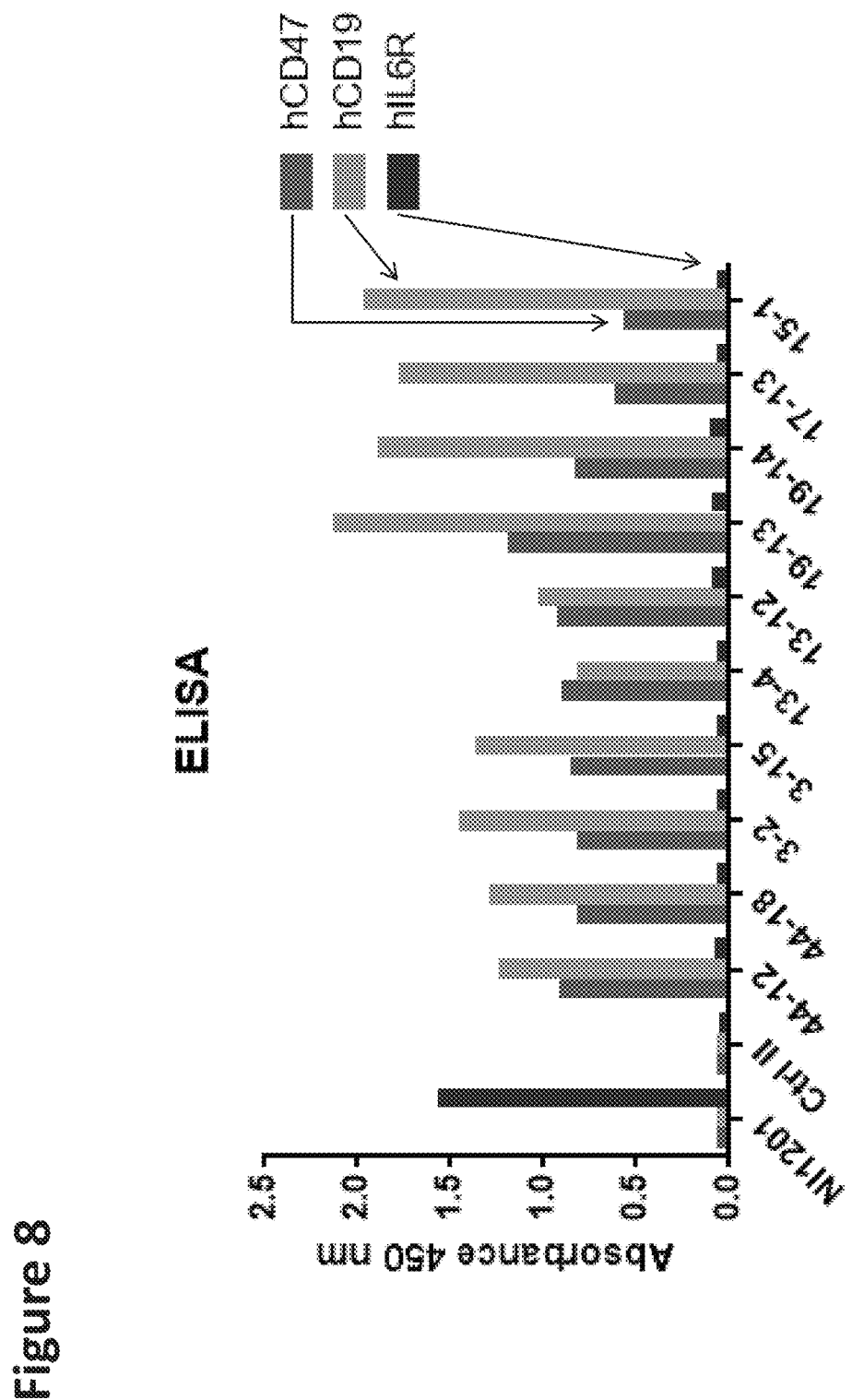
FIG. 8 is a graph depicting the results of an ELISA showing the specific binding of each arm of the bispecific antibody against two targets (hCD19 and hCD47) as well as an irrelevant control protein (hIL6R).

In order to confirm the specific binding against their targets, all candidates were evaluated for binding to hCD19 and hCD47 by ELISA (FIG. 8). The two specific targets of the bispecific antibodies and an irrelevant protein at 2 μg/mL in PBS were coated overnight at 4° C. In 96-well streptavidin-coated microplate. After 3 wash with PBS 0.05% (v/v) Tween (PBST), purified antibodies, diluted at 2 μg/mL in PBST 1% BSA, were incubated 30 min at 37° C. in the plate. Wells were washed 3 times with MST, and then a secondary antibody (anti human IgG Fc coupled to horseradish peroxidase) was added and incubated 1 h at 37° C. Tetramethylbenzidine was used to reveal ELISA and was blocked with sulfuric acid. Absorbance was read at 450 nm.

The expression of each candidate was scaled up and supernatants were harvested after 10 days and clarified by centrifugation at 1,300 g for 10 min. The purification process was composed of three affinity steps. First, the CaptureSelect IgG-CH1 affinity matrix (Life Technologies) was washed with PBS and then added to the clarified supernatant. After incubation overnight at 4° C., supernatants were centrifuged at 1,000 g for 10 min, the supernatant was discarded and the resin washed twice with PBS. Then, the resin was transferred to spin columns and a solution containing 50 mM glycine at pH 2.7 was used for elution.

Several elution fractions were collected, pooled and desalted against PBS using 50 kDa Amicon Ultra Centrifugal filter units (Merck KGaA). The final product, containing total human IgG from the supernatant, was quantified using a Nanodrop spectrophotometer (NanoDrop Technologies, Wilmington, Del.) and incubated for 15 min at RT and 20 rpm with the appropriate volume of KappaSelect affinity resin (GE Healthcare). Incubation, resin recovery, elution and desalting steps were performed as described previously (Fischer et al., Nature Comms. 2015). The last affinity purification step was performed using the LambdaFabSelect affinity resin. Total IgG, bispecific antibody percentage measured by HIC and purified bispecific productivity from CHO cell pools are summarized in Table 3. The data shows that deoptimization and reduced expression of the lambda chain leads to an increase of total IgG productivity and bispecific product. The optimization method generated an increase in yield of bispecific antibody of 2.5-fold.

What is claimed is:

1. A method to increase production yield of a protein complex that comprises more than one polypeptide, the method comprising:
    (a) providing more than one nucleic acid molecules encoding the polypeptides in the protein complex, wherein the protein complex is a multispecific antibody or a bispecific antibody;
    (b) introducing the nucleic acid molecule(s) into a cell;
    (c) culturing the cell under conditions that allow for the expression of polypeptides in the protein complex; and
    (d) decreasing expression of at least one of the polypeptides in the protein complex by modifying transcription rate, by modifying translation rate, by modifying mRNA stability, by modifying mRNA secondary structure, or by modifying any combination of these factors,
    wherein the production yield of the protein complex is increased compared to when the expression of at least one of the polypeptides is not decreased.

2. The method of claim 1, wherein the reduction in expression of one of the polypeptides in the protein complex is achieved by modifying transcription rate, translation rate, or mRNA stability.

3. The method of claim 1, wherein the reduction in expression of one of the polypeptides in the protein complex is achieved by modifying mRNA secondary structure.

4. The method of claim 1, wherein the reduction in expression of one of the polypeptides in the protein complex is achieved by modifying translation rate, by altering the codon composition of that polypeptide.

5. The method of claim 4, wherein the reduction in expression of one of the polypeptides in the protein complex is achieved by modifying translation rate, by altering the codon composition of that polypeptide via the replacement of certain codons with codons that are less frequently used in the host cell that is used for expression of the protein complex.

6. The method of claim 5, wherein the reduction in expression of one of the polypeptides in the protein complex is achieved by modifying translation rate, by altering the codon composition of that polypeptide via the replacement of certain codons with codons that are less frequently used in a mammalian host cell used for expression of the protein complex.

7. The method of claim 1, wherein the protein complex is a multispecific antibody.

8. The method of claim 1, wherein the protein complex is a bispecific antibody.

9. The method of claim 8, wherein the bispecific antibody is composed of two different light chains and a common heavy chain.

10. The method of claim 1, wherein more than one protein complex is co-expressed.

11. The method of claim 10, wherein the protein complexes are antibodies, and wherein more than one antibody is co-expressed.

* * * * *

SEQUENCE LISTING

```
<160> NUMBER OF SEQ ID NOS: 14

<210> SEQ ID NO 1
<211> LENGTH: 1395
<212> TYPE: DNA
<213> ORGANISM: Artificial Sequence
<220> FEATURE:
<223> OTHER INFORMATION: chemically synthesized

<400> SEQUENCE: 1
atggaatgga gctgggtctt tctcttcttc ctgtcagtaa ctacaggtgt ccactccgag      60
gtgcagctgt tggagtctgg gggaggcttg gtacagcctg gggggtccct gagactctcc     120
tgtgcagcct ctggattcac ctttagcagc tatgccatga gctgggtccg ccaggctcca     180 gggaagggc tggagtgggt ctcagctatt agtggtagtg gtggtagcac atactacgca      240
gactccgtga agggccggtt caccatctcc agagacaatt ccaagaacac gctgtatctg     300
caaatgaaca gcctgagagc cgaggacacg gccgtatatt actgtgcgaa aagttatggt     360
gcttttgact actggggcca gggaaccctg gtcacagtct cgagcgcctc caccaagggc     420
ccatcggtct tccccctggc accctcctcc aagagcacct ctgggggcac agcggccctg     480
ggctgcctgg tcaaggacta cttccccgaa ccggtgacag tctcgtggaa ctcaggagcc     540
ctgaccagcg gcgtgcacac cttcccggct gtcctacagt cctcaggact ctactccctc     600
agcagcgtgg tgactgtgcc ctccagcagc ttgggcaccc agacctacat ctgcaacgtg     660
aatcacaagc ccagcaacac caaggtggac aagagagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caagggcag    1080 ccccgagaac cacaggtgta taccctgccc ccatctcggg aggagatgac caagaaccag    1140
gtcagcctga cttgcctggt caaaggcttc tatcccagcg acatcgccgt ggagtgggag    1200
agcaacgggc agccggagaa caactacaag accacgcctc ccgtgctgga ctccgacggc    1260
tccttcttcc tctatagcaa gctcaccgtg gacaagtcca ggtggcagca ggggaacgtc    1320
ttctcatgct ccgtgatgca tgaggctctg cacaaccact acacgcagaa gagcctctcc    1380
ctgtctccgg gttaa                                                    1395

<210> SEQ ID NO 2
<211> LENGTH: 1395
<212> TYPE: DNA
<213> ORGANISM: Artificial Sequence
<220> FEATURE:
<223> OTHER INFORMATION: chemically synthesized
```

<400> SEQUENCE: 2

```
atggaatggt cctgggtgtt cctgttcttc ctgtccgtga ccaccggcgt ccactccgag      60
gtgcagctgc tggaatctgg cggcggactg gtccagcctg gaggctccct gagactgtct     120
tgcgccgcct ccggcttcac cttctccagc tacgccatgt cctgggtgcg acaggcccct     180
ggcaagggac tggaatgggt gtccgccatc tccggctccg gcggtctcta ctactacgcc     240
gactccgtga agggccggtt caccatctcc cgggacaact ccaagaacac cctgtacctg     300
cagatgaact ccctgcgggc cgaggacacc gccgtgtact actgcgccaa gtcctacggc     360
gccttcgact actggggcca gggcaccctg gtgacagtgt cctccgcctc caccaagggc     420
ccatccgtgt tccctctggc cccttccagc aagtccacct ggcggaaac cgctgccctg     480
ggctgcctgg tgaaagacta cttccccgag ccgtgaccg tgtcctggaa ctctggcgcc      540
ctgaccagcg gagtgcacac cttccctgcc gtgctgcagt cctccggcct gtactccctg     600
tcctccgtgg tgaccgtgcc ctccagctct ctgggcaccc agacctacat ctgcaacgtg     660
aaccacaagc cctccaacac caaggtggac aagcgggtgg aacccaagtc ctgcgacaag     720
acccacacct gtcctccctg ccctgcccct gaactgctgg gcggaccctc cgtgtttctg     780
ttccccccaa gcccaaggac accctgatga tctcccggac ccccgaagt gacctgcgtg     840
gtggtggacg tgtcccacga ggaccctgaa gtgaagttca attggtacgt ggacggcgtg     900
gaagtgcaca acgccaagac caagcccaga gaggaacagt acaactccac ctatcgggtg     960
gtgtctgtgc tgaccgtgct gcaccaggac tggctgaacg gcaaagagta caagtgcaag    1020
gtctccaaca aggccctgcc tgccccatc gaaaagacca tctccaaggc caagggccag     1080
ccccgcgaac cccaggtcta cactgcca cctagccggg aagagatgac caagaaccag      1140
gtgtccctga cctgtctggt gaaaggcttc tacccctccg atatcgccgt ggaatgggag    1200
tccaacggcc agcccgagaa caactacaag accaccccc ctgtgctgga ctccgacggc     1260
tcattcttcc tgtactccaa gctgaccgtg gacaagtccc ggtggcagca gggcaacgtg    1320
ttctcctgca gcgtgatgca cgaggccctg cacaaccact acacccagaa gtccctgtcc    1380
ctgagccccg gctaa                                                      1395
```

<210> SEQ ID NO 3
<211> LENGTH: 708
<212> TYPE: DNA
<213> ORGANISM: Artificial Sequence
<220> FEATURE:
<223> OTHER INFORMATION: chemically synthesized

<400> SEQUENCE: 3

```
atgagtgtgc ccactcaggt cctggggttg ctgctgctgt ggcttacaga tgccagatgt      60
gacatccaga tgacccagtc tccatcctcc ctgtctgcat ctgtaggaga cagagtcacc     120
atcacttgcc aggcgagtca gtccattagt agttatttaa attggtatca gcagaaacca     180
gggaaagccc ctaagctcct gatctacgct gcatcctcgt tggaaacagg ggtcccatca     240
aggttcagtg aagtggatc tgggacagat tttactttca ccatcagcag cctgcagcct     300
gaagatattg caacatatta ctgtcagcag aagcaccccc gggggccgag gaccttcggc     360
caagggacca aggtggaaat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
```

```
caggagagtg tcacagagca ggacagcaag acagcacct acagcctcag cagcaccctg    600
acgctgagca agcagacta cgagaaacac aaagtctacg cctgcgaagt cacccatcag    660
ggcctgagct cgcccgtcac aaagagcttc aacaggggag agtgttaa                708
```

```
<210> SEQ ID NO 4
<211> LENGTH: 708
<212> TYPE: DNA
<213> ORGANISM: Artificial Sequence
<220> FEATURE:
<223> OTHER INFORMATION: chemically synthesized

<400> SEQUENCE: 4
```

```
atgtccgtgc ccacccaggt gctgggactg ctgctgctgt ggctgaccga cgccagatgc    60
gacatccaga tgacccagag cccttccagc ctgagcgcct ccgtgggcga cagagtgacc    120
atcacctgtc aggcctccca gtccatctcc tcctacctga ctggtatca gcagaagccc    180 ggcaaggccc ctaagctgct gatctacgcc gcctcctccc tggaaaccgg cgtgccctcc    240
agattctccg gctccggctc tggcaccgac ttcaccttca ccatctccag cctgcagccc    300
gaggatatcg ccacctacta ctgccagcag aagcaccctc ggggccctag aaccttcggc    360
cagggcacca aggtggaaat caagcggacc gtggccgctc cctccgtgtt catcttccca    420
ccctccgacg agcagctgaa gtccggcacc gccagcgtcg tgtgcctgct gaacaacttc    480
tacccacgcg aggccaaggt gcagtggaag gtggacaacg ccctgcagtc cggcaactcc    540
caggaatccg tcaccgagca ggactccaag gacagcacct actccctgtc ctccaccctg    600
accctgtcca aggccgacta cgagaagcac aaggtgtacg cctgcgaagt gacccaccag    660
ggcctgtcca gccccgtgac caagtccttc aaccggggcg agtgctaa                708
```

```
<210> SEQ ID NO 5
<211> LENGTH: 717
<212> TYPE: DNA
<213> ORGANISM: Artificial Sequence
<220> FEATURE:
<223> OTHER INFORMATION: chemically synthesized

<400> SEQUENCE: 5
```

```
atgagtgtgc ccactcaggt cctggggttg ctgctgctgt ggcttacaga tgccagatgc    60
aattttatgc tgactcagcc ccactctgtg tcggagtctc cggggaagac ggtaaccatc    120
tcctgcaccc gcagcagtgg ctctatcgaa gataagtatg tgcagtggta ccagcagcgc    180
ccgggcagtt cccccaccat tgtgatctat tatgataacg aaagaccctc tggggtccct    240
gatcggttct ctggctccat cgacagctcc tccaactctg cctccctcac catctctgga    300
ctgaagactg aggacgaggc tgactactac tgtcagacct acgaccagag cctgtatggt    360
tgggtgttcg gcggagggac caagctgacc gtcctaggtc agcccaaggc tgccccctcg    420
gtcactctgt tcccgccctc ctctgaggag cttcaagcca acaaggccac actggtgtgt    480
ctcataagtg acttctaccc gggagccgtg acagtggctt ggaaagcaga tagcagcccc    540
gtcaaggcgg gagtggagac caccacaccc tccaaacaaa gcaacaacaa gtacgcggcc    600
agcagctatc tgagcctgac gcctgagcag tggaagtccc acagaagcta cagctgccag    660
gtcacgcatg aagggagcac cgtggagaag acagtggccc ctacagaatg ttcataa      717
```

```
<210> SEQ ID NO 6
<211> LENGTH: 717
<212> TYPE: DNA
<213> ORGANISM: Artificial Sequence
```

<220> FEATURE:
<223> OTHER INFORMATION: chemically synthesized

<400> SEQUENCE: 6

| | | | | | |
|---|---|---|---|---|---|
| atgtccgtgc | ctacccaggt | gctgggcctg | ctgctgctgt | ggctgaccga | cgcccggtgc | 60 |
| aacttcatgc | tgacccagcc | ccactccgtg | tccgagtccc | caggcaagac | cgtgaccatc | 120 |
| tcctgcaccc | ggtcctccgg | ctccatcgag | gacaaatacg | tgcagtggta | tcagcagcgg | 180 |
| cctggctcct | ccctaccat | cgtgatctac | tacgacaacg | agcggccctc | cggcgtgccc | 240 |
| gaccggttct | ctggctctat | cgactcctcc | tccaactccg | cctccctgac | catcagcggc | 300 |
| ctgaaaaccg | aggacgaggc | cgactactac | tgccagacct | acgaccagtc | cctgtacggc | 360 |
| tgggtgttcg | gcggaggcac | caagctgacc | gtcctaggtc | aacccaaggc | cgctccctcc | 420 |
| gtgaccctgt | tccctccatc | ctccgaggaa | ctgcaggcca | caaggccac | cctggtctgc | 480 |
| ctgatctccg | acttctaccc | tggcgccgtg | accgtggcct | ggaaggccga | cagctctcct | 540 |
| gtgaaggccg | gcgtggaaac | caccacccct | tccaagcagt | ccaacaacaa | atacgccgcc | 600 |
| tcctcctacc | tgtccctgac | ccctgagcag | tggaagtccc | accggtccta | cagctgccag | 660 |
| gtcacacacg | agggctccac | cgtggaaaag | accgtggccc | ctaccgagtg | ctcctaa | 717 |

<210> SEQ ID NO 7
<211> LENGTH: 717
<212> TYPE: DNA
<213> ORGANISM: Artificial Sequence
<220> FEATURE:
<223> OTHER INFORMATION: chemically synthesized

<400> SEQUENCE: 7

| | | | | | |
|---|---|---|---|---|---|
| atgtccgtgc | ctacccaggt | cttaggcctt | ctgctgctct | ggttgacaga | cgcccggtgc | 60 |
| aacttcatgc | tgactcagcc | ccacagtgtt | agcgagtctc | cgggaaagac | cgtgacaatc | 120 |
| tcatgtacta | gatcctctgg | gagcattgag | gacaaatacg | tacagtggta | tcagcaaagg | 180 |
| cccggtagtt | cgccaaccat | cgtgatatat | tacgataatg | aacgcccttc | cggcgtccca | 240 |
| gatcgttttt | caggatctat | tgactccagt | agcaactctg | cttcactaac | gatcagcggg | 300 |
| ctcaagacag | aggacgaagc | agattactac | tgccagacct | acgatcaatc | cctgtatggc | 360 |
| tgggtgttcg | gtggcggaac | taagctgacc | gtcctaggtc | aacccaaagc | cgctccttct | 420 |
| gttactttgt | ttcccccaag | tagcgaggaa | cttcaggcca | caaggcaac | actcgtgtgt | 480 |
| ctgatctccg | acttctatcc | tggggcggtt | accgtggcct | ggaaagctga | tagctctcca | 540 |
| gtaaaggcag | gcgtcgagac | aaccactccc | tcaaagcagt | ccaacaacaa | atacgccgct | 600 |
| tcgagctatc | tgtctttgac | gcctgaacag | tggaagagtc | atcgaagcta | ctcatgccaa | 660 |
| gtgacccacg | agggatctac | agtcgagaaa | accgtggctc | caactgagtg | ttcctaa | 717 |

<210> SEQ ID NO 8
<211> LENGTH: 717
<212> TYPE: DNA
<213> ORGANISM: Artificial Sequence
<220> FEATURE:
<223> OTHER INFORMATION: chemically synthesized

<400> SEQUENCE: 8

| | | | | | |
|---|---|---|---|---|---|
| atgagtgtac | cgactcaagt | acttgggctt | cttcttcttt | ggcttaccga | cgcacgttgc | 60 |
| aacttcatgc | ttactcaacc | gcactcagta | tcagagtcac | cggggaaaac | tgtaaccata | 120 |
| tcatgcactc | gtagcagtgg | gagcatagag | gacaaatacg | tccaatggta | tcaacaacgt | 180 |

```
ccggggtcat caccgaccat agtcatatat tacgacaacg aacgtccgtc aggtgtaccg    240
gatcgtttct caggttcaat agactcatca agcaacagcg cctcactcac catatcaggg    300
cttaaaaccg aggacgaagc cgactactat tgccaaactt acgaccaaag cctctacgga    360
tgggtattcg ggggtggtac aaaacttact gtcctaggtc aaccgaaagc agcaccgtca    420 gtaacactt ttccgccgtc atcagaggaa ctccaagcaa acaaagcaac cctcgtatgc     480
ctcatatcag acttctatcc ggggcagta accgtagcat ggaaagcaga ttcatcaccg     540
gtcaaagcag gggtagaaac taccaccccg tcaaagcaga gcaacaacaa atacgcagca    600
agctcatacc tcagccttac cccggaacaa tggaaatcac accgtagcta ctcatgccaa    660
gtaacccacg aagggtcaac cgtagaaaaa actgtagcac cgaccgagtg cagctaa      717
```

<210> SEQ ID NO 9
<211> LENGTH: 717
<212> TYPE: DNA
<213> ORGANISM: Artificial Sequence
<220> FEATURE:
<223> OTHER INFORMATION: chemically synthesized

<400> SEQUENCE: 9

```
atgtcggttc cgacgcaagt attagggctc ctattactat ggttaacgga cgcgcgttgc     60
aacttcatgt taacgcaacc gcattcggta tcggaatcgc cggggaaaac ggttacgata    120
tcgtgtacgc gttcgtcggg ctcgatagag acaaatacg tccaatggta tcaacaacgt     180
ccggggtcgt cgccgacgat agtcatatat tacgataacg aacgtccgtc gggtgtaccg    240
gatcgttttt cgggttcaat agattcgtcg tcgaactcgg cgagtctaac gatatcgggg    300
ctaaaaacgg aagatgaggc ggactattac tgccaaacgt acgaccaatc gctctacgga    360
tgggtattcg gtggtggaac gaaactaacg gtcctaggtc aaccgaaagc ggcaccgtcg    420
gttacgctat ttccgccgtc gtcggaagaa ttacaagcga acaaagcgac gctcgtctgc    480
ctcatatcgc attttttatcc gggtgcagta acgtagcgt ggaaagcgga ttcgtcgccg    540
gtcaaagcgg gtgtagaaac gacgacgccg tcgaagcaat cgaacaacaa atatgcggcg    600
tcgtcatacc tatcgctaac gccggaacaa tggaaatcgc atcgttcgta ttcgtgccaa    660
gtaacgcatg aagggtcgac ggtagaaaaa acggtagcgc cgacggaatg ttcgtaa      717
```

<210> SEQ ID NO 10
<211> LENGTH: 786
<212> TYPE: DNA
<213> ORGANISM: Artificial Sequence
<220> FEATURE:
<223> OTHER INFORMATION: chemically synthesized

<400> SEQUENCE: 10

```
cgcgctctag accagcgctg ccgccaccat gagtgtgccc actcaggtcc tggggttgct     60
gctgctgtgg cttacagatg ccagatgcaa ttttatgctg actcagcccc actctgtgtc    120
ggagtctccg gggaagacgg taaccatctc ctgcaccccg agcagtggct ctatcgaaga    180
taagtatgtg cagtggtacc agcagcgccc gggcagttcc ccaccattg tgatctatta     240 tgataacgaa agaccctctg ggtccctga tcggttctct ggctccatcg acagctcctc     300
caactctgcc tccctcacca tctctggact gaagactgag gacgaggctg actactactg    360
tcagacctac gaccagagcc tgtatggttg ggtgttcggc ggagggacca agctgaccgt    420
cctaggtcag cccaaggctg ccccctcggt cactctgttc ccgccctcct ctgaggagct    480
tcaagccaac aaggccacac tggtgtgtct cataagtgac ttctacccgg gagccgtgac    540
```

```
agtggcttgg aaagcagata gcagccccgt caaggcggga gtggagacca ccacaccctc    600
caaacaaagc aacaacaagt acgcggccag cagctatctg agcctgacgc ctgagcagtg    660
gaagtcccac agaagctaca gctgccaggt cacgcatgaa gggagcaccg tggagaagac    720
agtggcccct acagaatgtt cataatgagt ttaaacccgc cggcaaatcg atgaattcaa    780
attgat                                                               786
```

<210> SEQ ID NO 11
<211> LENGTH: 771
<212> TYPE: DNA
<213> ORGANISM: Artificial Sequence
<220> FEATURE:
<223> OTHER INFORMATION: chemically synthesized

<400> SEQUENCE: 11

```
cgcgtgcgct gccgccacca tgtccgtgcc tacccaggtg ctgggcctgc tgctgctgtg     60
gctgaccgac gcccggtgca acttcatgct gacccagccc cactccgtgt cggagtcccc    120
aggcaagacc gtgaccatct cctgcacccg tcctcggct ccatcgagga caaatacgtg    180
cagtggtatc agcagcggcc tggctccttc ccctaccatc gtgatctact acgacaacga    240
gcggccctcc ggcgtgcccg accggttctc tggctctatc gactcctcct ccaactccgc    300
ctccctgacc atcagcggcc tgaaaaccga ggacgaggcc gactactact gccagaccta    360
cgaccagtcc ctgtacggct gggtgttcgg cggaggcacc aagctgaccg tcctaggtca    420
acccaaggcc gctcccctccg tgaccctgtt ccctccatcc tccgaggaac tgcaggccaa    480
caaggccacc ctggtctgcc tgatctccga cttctaccct ggcgccgtga ccgtggcctg    540
gaaggccgac agctctcctg tgaaggccgg cgtggaaacc accaccccctt ccaagcagtc    600 caacaacaaa tacgccgcct cctcctacct gtccctgacc cctgagcagt ggaagtccca    660
ccggtcctac agctgccagg tcacacacga gggctcacc gtggaaaaga ccgtggcccc    720
taccgagtgc tcctaatgag tttaaacccg ccggcaaatc gataaattga t              771
```

<210> SEQ ID NO 12
<211> LENGTH: 786
<212> TYPE: DNA
<213> ORGANISM: Artificial Sequence
<220> FEATURE:
<223> OTHER INFORMATION: chemically synthesized

<400> SEQUENCE: 12

```
cgcgctctag accagcgctg ccgccaccat gtccgtgcct acccaggtct taggccttct     60
gctgctctgg ttgacagacg cccggtgcaa cttcatgctg actcagcccc acagtgttag    120
cgagtctccg ggaaagaccg tgacaatctc atgtactaga tcctctggga gcattgagga    180
caaatacgta cagtggtatc agcaaaggcc cggtagttcg ccaaccatcg tgatatatta    240
cgataatgaa cgcccttccg gcgtcccaga tcgtttttca ggatctattg actccagtag    300
caactctgct tcactaacga tcagcgggct gaagacagag gacgaagcag attactactg    360
ccagacctac gatcaatccc tgtatggctg ggtgttcggt ggcggaacta agctgaccgt    420
cctaggtcaa cccaaagccg ctccttctgt tactttgttt ccgccaagta gcgaggaact    480
tcaggccaac aaggcaacac tcgtgtgtct gatctccgac ttctatcctg ggcggttac    540 cgtggcctgg aaagctgata gctctccagt aaaggcaggc gtcgagacaa ccactccctc    600
aaagcagtcc aacaacaaat acgccgcttc gagctatctg tctttgacgc ctgaacagtg    660
```

| | |
|---|---|
| gaagagtcat cgaagctact catgccaagt gacccacgag ggatctacag tcgagaaaac | 720 |
| cgtggctcca actgagtgtt cctaatgagt ttaaacccgc cggcaaatcg atgaattcaa | 780 |
| attgat | 786 |

<210> SEQ ID NO 13
<211> LENGTH: 786
<212> TYPE: DNA
<213> ORGANISM: Artificial Sequence
<220> FEATURE:
<223> OTHER INFORMATION: chemically synthesized

<400> SEQUENCE: 13

| | |
|---|---|
| cgcgctctag accagcgctg ccgccaccat gagtgtaccg actcaagtac ttgggcttct | 60 |
| tcttctttgg cttaccgacg cacgttgcaa cttcatgctt actcaaccgc actcagtatc | 120 |
| agagtcaccg gggaaaactg taaccatatc atgcactcgt agcagtggga gcatagagga | 180 |
| caaatacgtc caatggtatc aacaacgtcc ggggtcatca ccgaccatag tcatatatta | 240 |
| cgacaacgaa cgtccgtcag gtgtaccgga tcgtttctca ggttcaatag actcatcaag | 300 |
| caacagcgcc tcactcacca tatcagggct aaaaccgag gacgaagccg actactattg | 360 |
| ccaaacttac gaccaaagcc tctacggatg gtattcgggg gtggtacaa aacttactgt | 420 |
| cctaggtcaa ccgaaagcag caccgtcagt aacactttttt ccgccgtcat cagaggaact | 480 |
| ccaagcaaac aaagcaaccc tcgtatgcct catatcagac ttctatccgg gggcagtaac | 540 |
| cgtagcatgg aaagcagatt catcaccggt caaagcaggg gtagaaacta ccaccccgtc | 600 |
| aaagcagagc aacaacaaat acgcagcaag ctcataccct agccttaccc cggaacaatg | 660 |
| gaaatcacac cgtagctact catgccaagt aacccacgaa gggtcaaccg tagaaaaaac | 720 |
| tgtagcaccg accgagtgca gctaatgagt ttaaacccgc cggcaaatcg atgaattcaa | 780 |
| attgat | 786 |

<210> SEQ ID NO 14
<211> LENGTH: 786
<212> TYPE: DNA
<213> ORGANISM: Artificial Sequence
<220> FEATURE:
<223> OTHER INFORMATION: chemically synthesized

<400> SEQUENCE: 14

| | |
|---|---|
| cgcgctctag accagcgctg ccgccaccat gtcggttccg acgcaagtat tagggctcct | 60 |
| attactatgg ttaacggctg cgcgttgcaa cttcatgtta acgcaaccgc attcggtatc | 120 |
| ggaatcgccg gggaaaacgg ttacgatatc gtgtacgcgt tcgtcgggct cgatagagga | 180 |
| caaatacgtc caatggtatc aacaacgtcc ggggtcgtcg ccgacgatag tcatatatta | 240 |
| cgataacgaa cgtccgtcgg gtgtaccgga tcgttttttcg ggttcaatag attcgtcgtc | 300 |
| gaactcggcg agtctaacga tatcggggct aaaaacggaa gatgaggcgg actactactg | 360 |
| ccaaacgtac gaccaatcgc tctacggatg gtattcggt ggtggaacga aactaacggt | 420 |
| cctaggtcaa ccgaaagcgg caccgtcggt tacgctatttt ccgccgtcgt cggaagaatt | 480 |
| acaagcgaac aaagcgacgc tcgtctgcct catatcggat tttttatccgg gtgcagtaac | 540 |
| ggtagcgtgg aaagcggatt cgtcgccggt caaagcgggg gtagaaacga cgacgccgtc | 600 |
| gaagcaatcg aacaacaaat atgcggcgtc gtcataccta tcgctaacgc cggaacaatg | 660 |

-continued

| | | | | | |
|---|---|---|---|---|---|
| gaaatcgcat | cgttcgtatt | cgtgccaagt | aacgcatgaa | gggtcgcagc | gaggagaaga | 720 |
| gagagggccg | acggaatgtt | cgtaatgagt | ttaaacccgc | cggcaaatcg | atgaattcaa | 780 |
| attgat | | | | | | 786 |